US005079342A

United States Patent [19]

Alizon et al.

[11] Patent Number: 5,079,342

[45] Date of Patent: Jan. 7, 1992

[54] CLONED DNA SEQUENCES RELATED TO THE ENTIRE GENOMIC RNA OF HUMAN IMMUNODEFICIENCY VIRUS II (HIV-2), POLYPEPTIDES ENCODED BY THESE DNA SEQUENCES AND USE OF THESE DNA CLONES AND POLYPEPTIDES IN DIAGNOSTIC KITS

[75] Inventors: Marc Alizon, Paris; Luc Montagnier, Le Pleissis Robinson; Denise Geutard, Paris, all of France; Francois Clavel, Rockville, Md.; Pierre Sonigo; Mireille Guyader, both of Paris, France

[73] Assignee: Institut Pasteur, Paris, France

[21] Appl. No.: 13,477

[22] Filed: Feb. 11, 1987

Related U.S. Application Data

[63] Continuation-in-part of Ser. No. 3,764, Jan. 16, 1987, which is a continuation-in-part of Ser. No. 933,184, Nov. 21, 1986, abandoned, which is a continuation-in-part of Ser. No. 916,080, Oct. 6, 1986, abandoned, and a continuation-in-part of Ser. No. 835,228, Mar. 3, 1986, Pat. No. 4,839,288.

[51] Int. Cl.[5] .......................... C07K 7/06; C07K 7/08; C07K 7/10; G01N 33/569

[52] U.S. Cl. .................................... 530/324; 530/326; 530/327; 530/328; 530/329; 435/5; 435/974

[58] Field of Search ........................... 435/5, 235, 974; 530/324, 326, 327–329

[56] References Cited

U.S. PATENT DOCUMENTS 4,629,783 12/1986 Cosand ............................... 530/324

FOREIGN PATENT DOCUMENTS

WO85/04897 7/1985 World Int. Prop. O. .

OTHER PUBLICATIONS

Clavel et al., "Isolation of a New Human Retrovirus from West African Patients with Aids", Science 233 (1986) 343–346.

Allan et al., "Major Glycoprotein Antigens that Induce Antibodies in Aids are Encoded by HTLV-III", Science 228 (1985) 1091–1094.

Chang et al. "Detection of Antibodies to Human T-Cell Lymphotropic Virus-III (HTLV-III) with an Immunoassay Employing a Recombinant *Escherichia coli*–Derived Viral Antigenic Peptide", Bio/Technology 3 (1985) 905–909.

P. J. Kanki et al.; "Isolation of T-Lymphotropic Retrovirus Related to HIV-III/LAV Form Wild-Caught African Green Monkeys"; Science, 230:951–954 (1985).

F. Clavel et al.; "LAV type II: un second retrovirus associe au Sida en Afrigue de l'Ouest"; Compte Rendus de l'Academie des Sciences Paris, Serie III, 302:485–488 (1986).

F. Barin et al.; "Serological Evidence for Virus Related to Simian T-Lymphotropic Retrovirus III in Residents of West Africa"; The Lancet, No. 8469/70, pp. 1387–1389 (1985).

P. J. Kanki et al.; "Serologic Identification and Characterization of a Macaque T-Lymphotropic Retrovirus Closely Related to HTLV-III"; Science, 228:1199–1201 (1985).

M. D. Daniel et al.; "Isolation of T-Cell Tropic HTLV-III-Like Retrovirus from Macaques"; Science, 228:1201–1203 (1985).

*Primary Examiner*—Christine Nucker

*Attorney, Agent, or Firm*—Finnegan, Henderson, Farabow, Garrett & Dunner

[57] ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

25 Claims, 5 Drawing Sheets

FIG. 1A

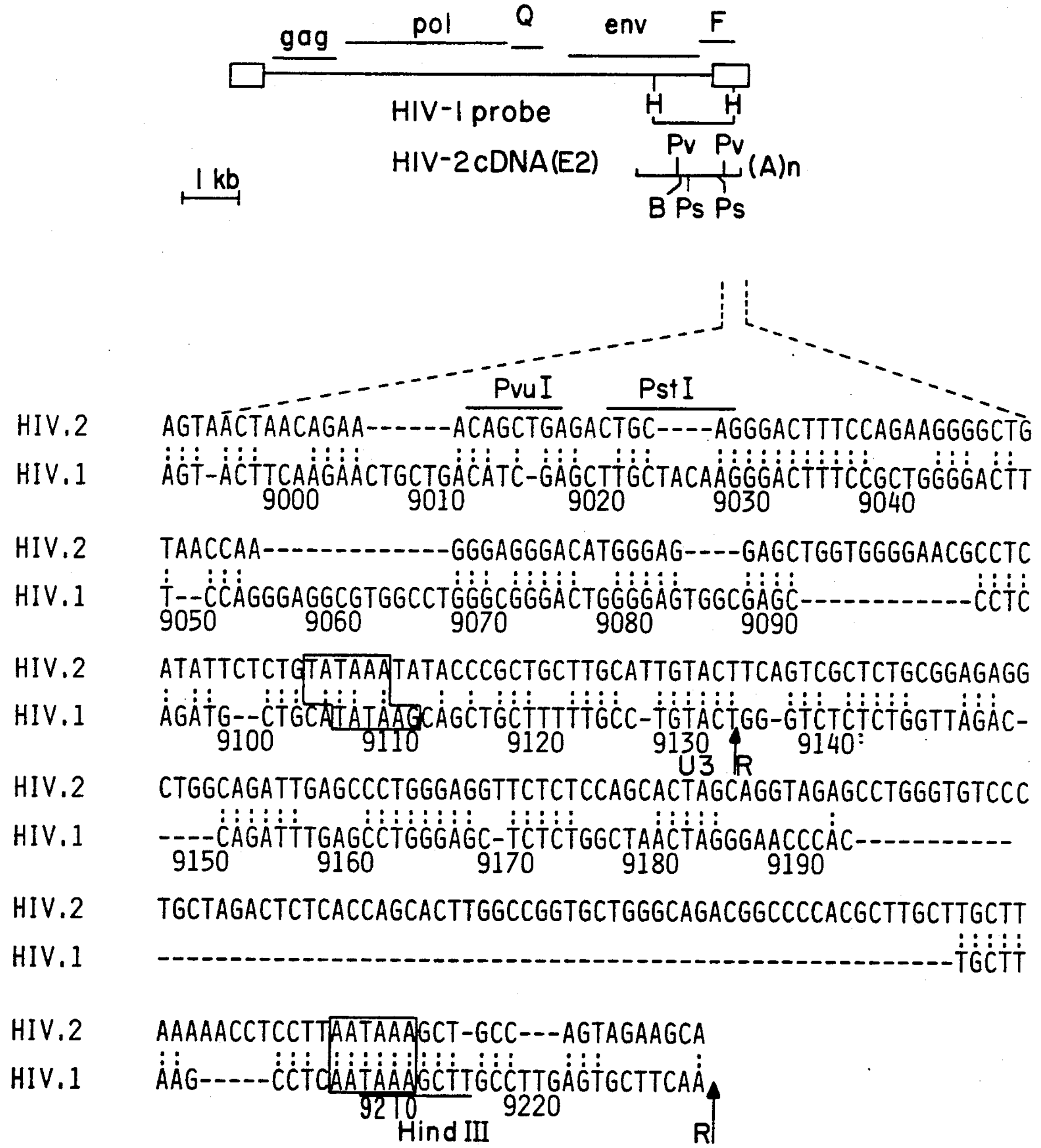

FIG. 1B

| | | | | | |
|---|---|---|---|---|---|
| | | | PvuI | PstI | |
| HIV.2 | AGTAACTAACAGAA------ACAGCTGAGACTGC----AGGGACTTTCCAGAAGGGGCTG |
| HIV.1 | AGT-ACTTCAAGAACTGCTGACATC-GAGCTTGCTACAAGGGACTTTCCGCTGGGGACTT |
| | 9000 9010 9020 9030 9040 |

| HIV.2 | TAACCAA-------------GGGAGGGACATGGGAG----GAGCTGGTGGGGAACGCCTC |
| HIV.1 | T--CCAGGGAGGCGTGGCCTGGGCGGGACTGGGGAGTGGCGAGC-----------CCTC |
| | 9050 9060 9070 9080 9090 |

| HIV.2 | ATATTCTCTG TATAAA TATACCCGCTGCTTGCATTGTACTTCAGTCGCTCTGCGGAGAGG |
| HIV.1 | AGATG--CTGCA TATAAG CAGCTGCTTTTTGCC-TGTACTGG-GTCTCTCTGGTTAGAC- |
| | 9100 9110 9120 9130 9140 |
| | U3 R |

| HIV.2 | CTGGCAGATTGAGCCCTGGGAGGTTCTCTCCAGCACTAGCAGGTAGAGCCTGGGTGTCCC |
| HIV.1 | ----CAGATTTGAGCCTGGGAGC-TCTCTGGCTAACTAGGGAACCCAC----------- |
| | 9150 9160 9170 9180 9190 |

| HIV.2 | TGCTAGACTCTCACCAGCACTTGGCCGGTGCTGGGCAGACGGCCCCACGCTTGCTTGCTT |
| HIV.1 | ---------------------------------------------------TGCTT |

| HIV.2 | AAAAACCTCCTT AATAAA GCT-GCC---AGTAGAAGCA |
| HIV.1 | AAG-----CCTC AATAAA GCTTGCCTTGAGTGCTTCAA |
| | 9210 9220 |
| | HindIII R |

FIG.2A
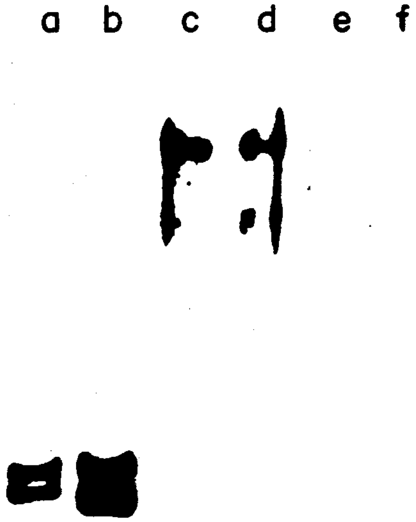
FIG.2B
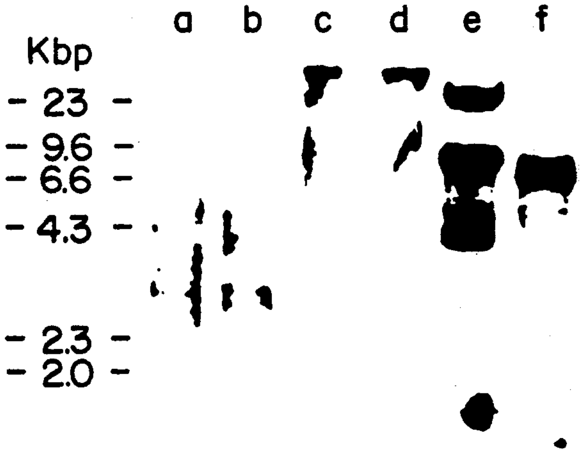
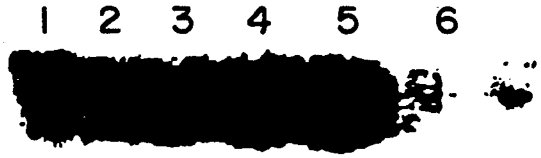
FIG.2C
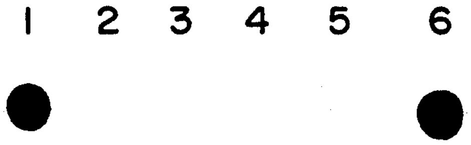
FIG.2D

CLONED DNA SEQUENCES RELATED TO THE ENTIRE GENOMIC RNA OF HUMAN IMMUNODEFICIENCY VIRUS II (HIV-2), POLYPEPTIDES ENCODED BY THESE DNA SEQUENCES AND USE OF THESE DNA CLONES AND POLYPEPTIDES IN DIAGNOSTIC KITS

BACKGROUND OF THE INVENTION

This application is a continuation-in-part of U.S. patent application Ser. No. 07/033,764, of Alizon et al. for "Cloned DNA Sequences Related to the Entire Genomic RNA of Human Immunodeficiency Virus II (HIV-2), Polypeptides Encoded by these DNA Sequences and Use of these DNA Clones and Polypeptides in Diagnostic Kits," filed Jan. 16, 1987 (now pending), which is a continuation-in-part of U.S. patent application Ser. No. 06/933,184 filed Nov. 21, 1986 (now abandoned), which is a continuation-in-part application of U.S. application Ser. No. 916,080 of Montagnier et al. for "Cloned DNA Sequences Related to the Genomic RNA of the Human Immunodeficiency Virus II (HIV-2), Polypeptides Encoded by these DNA Sequences and Use of these DNA Clones and Polypeptides in Diagonostic Kits," filed Oct. 6, 1986 (now abandoned) and U.S. patent application Ser. No. 835,228 of Montagnier et al. for "New Retrovirus Capable of Causing AIDS, Antigens Obtained from this Retrovirus and Corresponding Antibodies and their Application for Diagnostic Purposes," filed Mar. 3, 1986 (now U.S. Pat. No. 4,839,288, June 13, 1989). The disclosures of each of these predecessor applications are expressly incorporated herein by reference.

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II(-HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered int he course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection NMationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify viral DNA which may or may not be digested with restriction enzymes; (2) Northern blot techniques to identify viral RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by ultra-centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

In accordance with a further object of the present invention, a peptide is provided as described above, either alone or conjugated to a carrier molecule, the peptide being capable of eliciting the production of an antibody to the peptide, and said antibody is capable of forming an effective immunocomplex with the entire HIV-2 retrovirus or with its corresponding proteins.

To further achieve the objects of the invention, a vaccinating agent is provided which comprises at least one peptide selected from the polypeptide expression products of the viral DNA in admixture with suitable carriers, adjuvents stabilizers.

It is understood that both the foregoing general description and the following detailed decryption are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2.

FIG. 1A depicts the genetic organization of HIV-1, position of the HIV-1 HindIII fragment used as a probe to screen the cDNA library, and restriction map of the HIV-2 cDNA clone, E2.

FIG. 1B depicts the nucleotide sequence of the 3′ end of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. U.S.A. 80: 726–730 (1983), specifically incorporated herein by reference. The U3-R junction in HIV-1 is indicated and the poly A addition signal and potential TATA promoter regions are boxed. In FIG. 1A, the symbols B, H, Ps and Pv refer to the restriction sites BamHI, HindIII, PstK and PvuII, respectively.

FIG. 2 generally depicts the HIV-2 specificity of the E2 clone.

FIGS. 2A and B are line drawings representing Southern Blots of DNA extracted from CEM cells infected with the following isolates: HIV-$2_{ROD}$ (a,c), HIV-$2_{DUL}$ (b,d), and HIV-$1_{BRU}$ (e,f). DNA in lanes a,b,f was Pst I digested; in c,d,e DNA was undigested.

FIGS. 2C and D are line drawings representing dot blot hybridization of pelleted virions from CEM cells infected by the HIV-$1_{BRU}$(1), Simian Immunodeficiency Virus (SIV) isolate Mn 142-83 (3), HIV-$2_{DUL}$ (4), HIV-$2_{ROD}$ (5), and HIV-$1_{ELI}$ (6). Dot 2 is a pellet from an equivalent volume of supernatant from uninfected CEM. Thus, FIGS. 2A and C depict hybridization with the HIV-2 cDNA (E2) and FIGS. 2B and D depicts hybridization to an HIV-1 probe consisting of a 9Kb SacI insert from HIV-1 BRU(clone lambda J 19).

FIG. 3 generally depicts a restriction map of the HIV-2 ROD genome and its homology to HIV-1.

In FIG. 3A, the open boxes represent viral sequences, the LTR are filled, and the dotted boxes represent cellular flanking sequences (not mapped). Only some characteristic restriction enzyme sites are indicated. λROD 27 and λROD 35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

DETAILED DESCRIPTION OF THE PREFERRED EMBODIMENTS

Figure 3A:
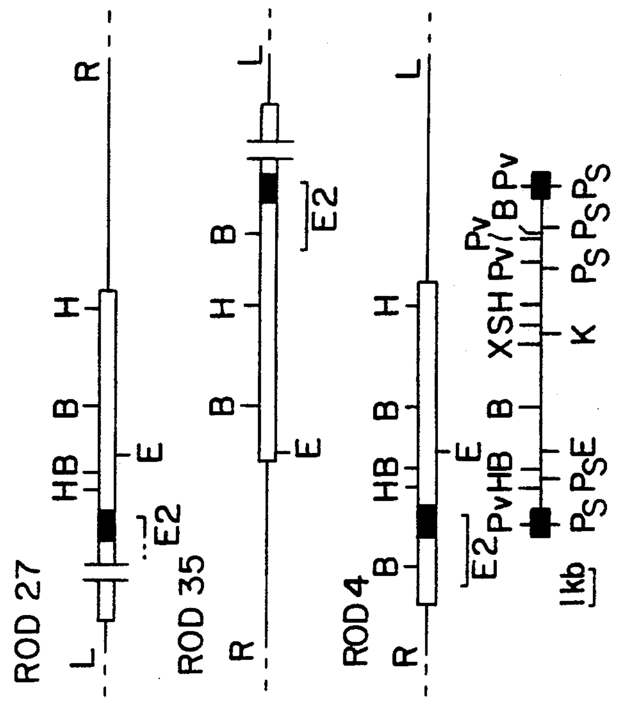
FIG. 3A specifically depicts the organization of three recombinant phage lambda clones, ROD 4, ROD 27, and ROD 35.

Reference will now be made in detail to the presently preferred embodiments of the invention, which, together with the following examples, serve to explain the principles of the invention.

The genetic structure of the HIV-2 virus has been analyzed by molecular cloning according to the method set forth herein and in the Examples. A restriction map of the genome of this virus is included in FIG. 5. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 0 and other human and simian retroviruses. From the totality of these data, diagnostic probes can be discerned and prepared.

Generally, to practice one embodiment of the present invention, a series of filter hybridizations of the HIB-2 RNA genome with probes derived from the complete cloned HIV-1 genome and from the gag and pol genes were conducted. These hydridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al., in Cancer 18: 522–529 (1965), specifically incorporated herein by reference. The CEM cells used were infected with the isolate ROD and were continuously producing high amounts of HIV-2.

After second-strand synthesis, the cDNAs were inserted into the M13 tb 130 bacteriophage vector. A collection of $10^4$ M13 recombinant phages was obtained and screened in situ with an HIV-1 probe spanning 1.5 kb. of the 3' of the $LAV_{BRU}$ isolate (depicted in FIG. 1A). Some 50 positive plaques were detected, purified, and characterized by end sequencing and cross-hybridizing the inserts. This procedure is sescribed in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundride insertions/deletions need to be introduced. In comparison, the homology of the corresponding domains in HIV-1 isolates from U.S.A. and Africa is greater than 95% and no insertions or deletions are seen.

The largest insert of this group of M13 clones was a 2 kb. clone designeated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIGS. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the oxogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization of HIV-1 infected cells only as depicted in FIG. 2, b.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with $HIV\text{-}2_{ROD}$.

About $2\times10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences and shown in FIG. 3, A.

Fragments of the lambda clones were subcloned into a plasmid vector p UC 18.

Plasmid pROD 27-5' is derived from λROD 27 and contains the 5' 2Kb of the HIV-2 genome and cellular flanking sequences (5' LTR and 5' viral coding sequences to the EcoRI site).

Plasmid pROD 4-8 is derivied from λROD 4 and contains the about 5Kb HindIII fragment that is the central part of the HIV-2 genome.

Plasmid pROD 27-5' and pROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamH1 and HindIII cloning sites.

Plasmid pROD 35 contains all the HIV-2 coding sequences 3' to the EcoRI site, the 3' LTR about 4 Kb of cellular flanking sequences.

Figure 5:
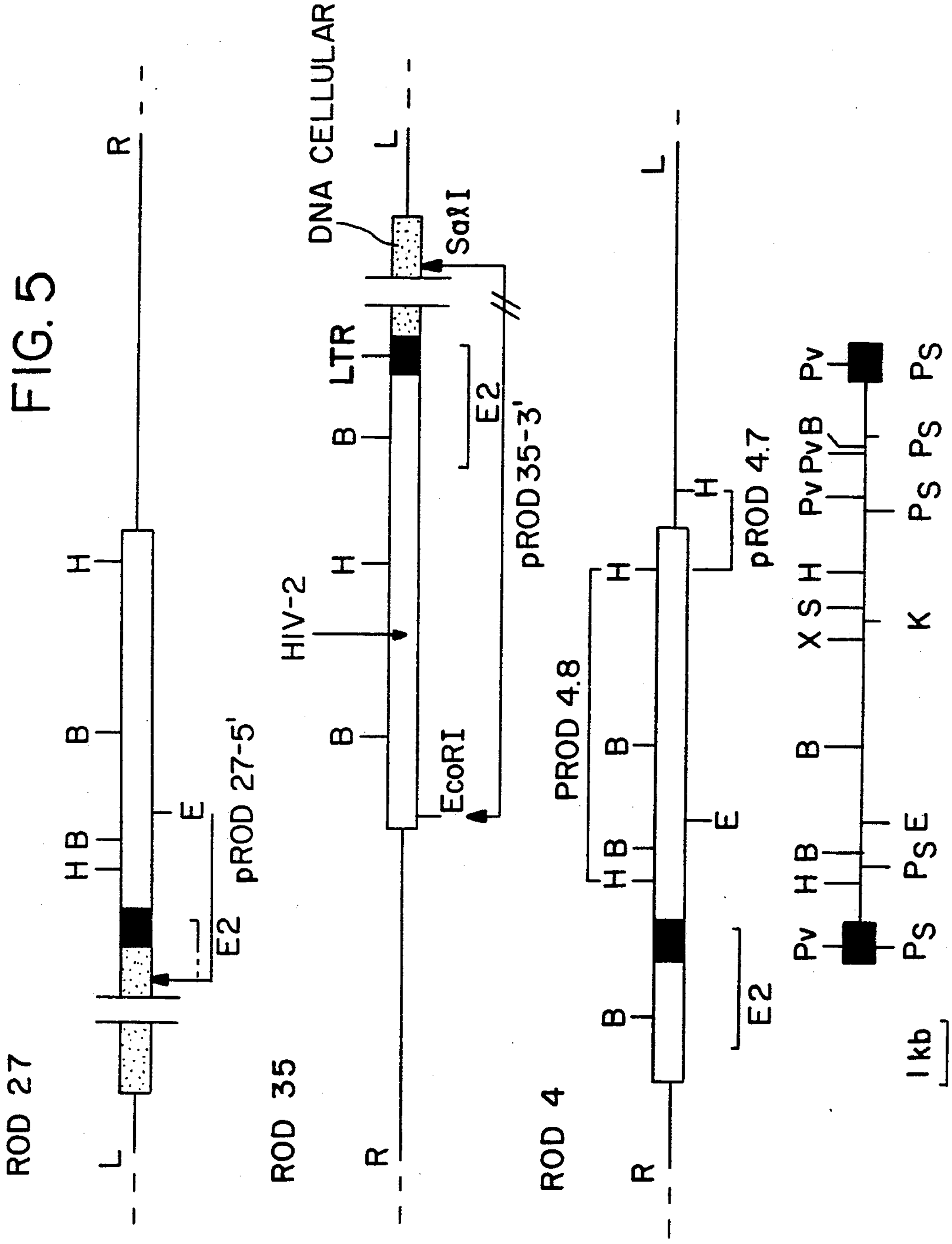
FIG. 5 depicts the position of derived plasmids from λROD 27, λROD 35 and λROD 4.

Plasmid pROD 27-5' and pROD 35 in *E. coli* strain HB 101 are depostied respectively under No. I-626 and I-633 at the CNCM, and have also been deposited at the NCIB (British Collection). These plasmids are depicted in FIG. 5. Plasmids pROD 4-7 and pROD 4-8 in *E. coli* strain TG1 are deposited respectively under No. I-627 and I-628 at the CNCM.

To reconstitute the complete HIV-2 ROD genome, pROD 35 is linearized with EcoRI and the EcoRI insert of pROD 27-5' is ligated in the correct orientation into this site.

Figure 3B:
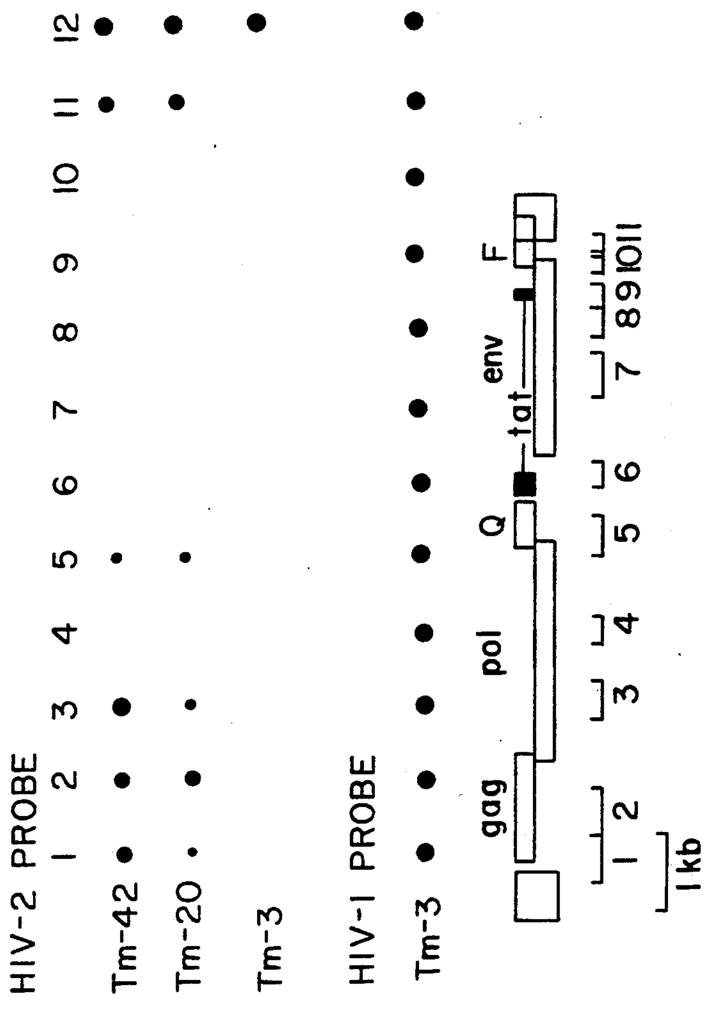
FIG. 3B specifically depicts dots 1-11 which correspond to the single-stranded DNA form of M13 subclones form the HIV-$1_{BRU}$ cloned geonome (λJ19). Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2x SSC, 0.1% SDS at 25 °C. (Tm −42° C.), 1x SSC, 0.1% SDS at 60° C. (Tm −20° C.), and 0.1x SSC, 0.1% SDS at 60° C. (Tm −3° C.) and exposed overnight. A duplicate dot blot was hybridized and washed in stringent conditions (as described in Example 2) with the labelled lambda J19 clone carrying the complete HIV-$1_{BRU}$ genome. HIV-1 and HIV-2 probes were labelled the same specific activity ($10^8$ cpm/g.).

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm-42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1, as are African isolates from Zaire described by Alizon et al., *Cell* 40:63–74 (1986).

It was observed that HIV-2 is related more closely to the Simian Immunodeficiency Virus (SIV) than it is to HIV-1. This correclation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the U.S.A. this simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV--$2_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4B:
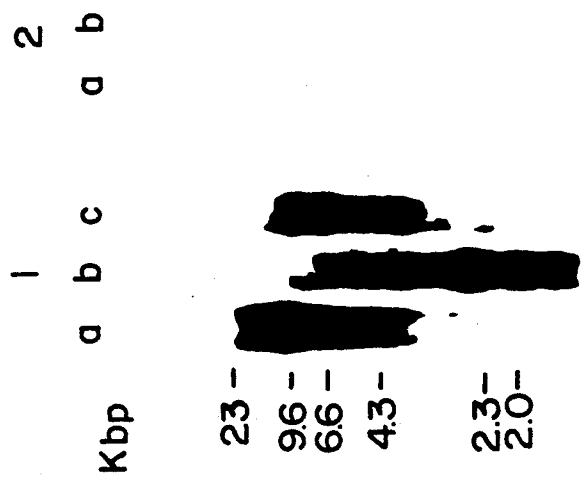
FIG. 4B is a line drawing depicting DNA from HUT 78 (a human T lymphoid cell line) cells infected with STLV3 MAC isolate Mm 142-83. The same amounts of DNA and enzymes were used as indicated in panel A. Hybridization was performed with the same probe as in A, but in non-stringent conditions. As described in Example 1 washing was for one hour in 2x SSC, 0.1% SDS at 40° C. (panel 1) and after exposure, the same filter was re-washed in 0.1x SSC, 0.1% SDS at 60° C. (panel 2). The autoradiographs were obtained after overnight exposition with intensifying screens.
Figure 4A:
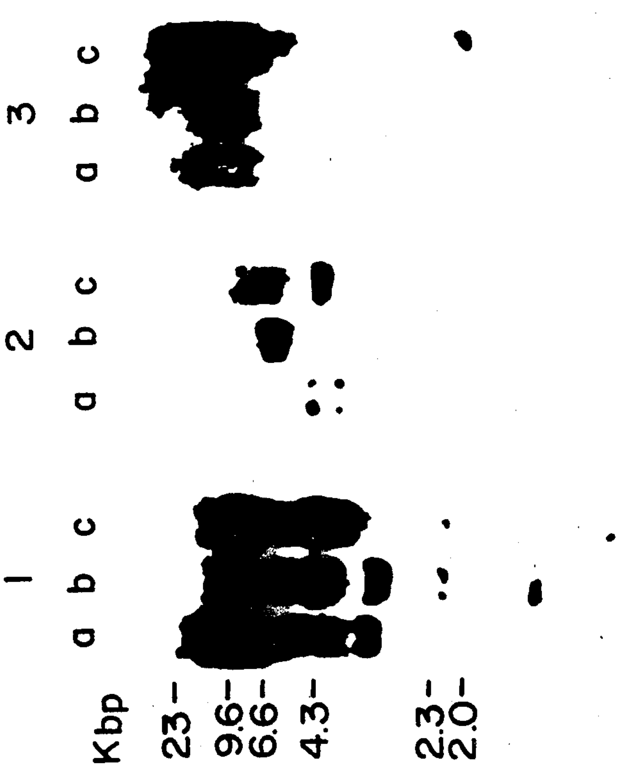
FIG. 4A is a line drawing depicting DNA (20 μg. per lane) from CEM cells infected by the isolate HIV-$2_{DUL}$ (panel 1) or peripheral blood lymphocytes (PBL) infected by the isolates HIV-$2_{GOM}$ (panel 2) and HIV- $2_{MIR}$ (panel 3) digested with: EcoRI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cmp/μg.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-$2_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit amino acid heterogeneities. See, for example, Clavel et al., *Nature* 324 (18):691–695 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could be used to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1: Cloning of a cDNA Complementary to Genomic RNA From HIV-2 Virions HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Gubler and Hoffman in Gene, 25: 263–269 (1983), specifically incorporated herein by reference, using a commercial cDNA synthesis kit obtained from Amersham. After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}p$ labelled to a specific activity of $10^9$cpm/μg. The filters were prehybridized in 5×SSC, 5×Denhardt solution, 25% formamide, and denatured salmon sperm DNA(100 μg/ml.) at 37° C. for 4 hours and hybridized for 16 hours in the same buffer (Tm −42° C.) plus $4\times10^7$ cpm of the labelled probe ($10^6$ cpm/ml. of hybridization buffer). The washing was done in 5×SSC, 0.1% SDS at 25° C. for 2 hours. 20×SSC is 3M Nacl, 0.3M Na citrate. Positive plaques were purified and single-stranded M13 DNA prepared and end-sequenced according to the method described in Proc. Nat'l. Acad. Sci. U.S.A., 74: 5463–5467 (1977) of Sanger et al.

Example 2: Hybridization of DNA from HIV-1 and HIV-2 Infected Cells and RNA from HIV-1 and 2 and SIV Virons With a Probe Derived From an HIV-2 Cloned cDNA DNA was extracted from infected CEM cells continuously producing HIV-1 or 2. The DNA digested with 20 μg of PstI or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity.

Prehybridization was done in 50% formamide, 5×SSC, 5×Denhardt solution, and 100 mg./ml. denatured salmon sperm DNA for 4 hours at 42° C. Hybridiazation was performed in the same buffer plus 10% Dextran sulphate, and $10^6$ cpm/ml. of the labelled E2 insert (specific activity $10^9$ cpm/μg.) for 16 hours at 42° C. Washing was in 0.1×SSC, 0.1% SDS for 2×30 mn. After exposition for 16 hours with intensifying screens, the Southern blot was dehybridized in 0.4N NaOH, neutralized, and rehybridized in the same conditions to the HIV-1 probe labelled to $10^9$ cpm/μg.

Example 3: Cloning in Lambda Phage of the Complete Provirus DNA of HIV-2

DNA from the HIV-$2_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques ($2\times10^6$) obtained after in vitro packaging and plating on *E. coli* LA 101 strain were screened insitu with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4: complete Genomic Sequence of the ROD HIV-2 Isolate

Experimental analysis of the HIV-2 ROD isolate yielded the following sequence which represents the complete genome of this HIV-2 isolate. Genes and major expression products identified within the following sequence are indicated by nucleotides numbered below:

1) GAG gene (546–2111) expresses a protein product having a molecular weight of around 55 Kd and is cleaved into the following proteins:
 a) p 16 (546–950)
 b) p 26 (951–1640)
 c) p 12 (1701–2111)
2) polymerase (1829–4936)
3) Q protein (4869–5513)
4) R protein (5682–5996)
5) X protein (5344–5679)
6) Y protein (5682–5996)
7) Env protein (6147–8720)
8) F protein (8557–9324)

9) TAT gene (5845–6140 and 8307–8400) is expressed by two exons separated by introns.

10) ART protein (6071–6140 and 8307–8536) is similarly the expression product of two exons.

11) LTR:R (1–173 and 9498–9671)

12) U5 (174–299)

13) U3 (8942–9497)

It will be known to one of skill in the art that the absolute numbering which has been adopted is not essential. For example, the nucleotide within the LTR which is designated as "1" is a somewhat arbitrary choice. What is important is the sequence information provided.

```
GGTCGCTCTGCGGAGAGGCTGGCAGATTGAGCCCTGGGAGGTTCTCTCCAGCACTAGCAG
         .         .         .         .         .         .

GTAGAGCCTGGGTGTTCCCTGCTAGACTCTCACCAGCACTTGGCCGGTGCTGGGCAGACG
         .         .         .        100        .         .

GCCCCACGCTTGCTTGCTTAAAAACCTCTTAATAAAGCTGCCAGTTAGAAGCAAGTTAAG
         .         .         .         .         .         .

TGTGTGCTCCCATCTCTCCTAGTCGCCGCCTGGTCATTCGGTGTTCACCTGAGTAACAAG
         .        200        .         .         .         .

ACCCTGGTCTGTTAGGACCCTTCTTGCTTTGGGAAACCGAGGCAGGAAAATCCCTAGCAG
         .         .         .         .         .        300

GTTGGCGCCTGAACAGGGACTTGAAGAAGACTGAGAAGTCTTGGAACACGGCTGAGTGAA
         .         .         .         .         .         .

GGCAGTAAGGGCGGCAGGAACAAACCACGACGGAGTGCTCCTAGAAAGGCGCGGGCCGAG
         .         .         .        400        .         .

GTACCAAAGGCAGCGTGTGGAGCGGGAGGAGAAGAGGCCTCCGGGTGAAGGTAAGTACCT
         .         .         .         .         .         .

ACACCAAAAACTGTAGCCGAAAGGGCTTGCTATCCTACCTTTAGACAGGTAGAAGATTGT
         .        500        .         .         .         .

      Met Gly Ala Arg Asn Ser Val Leu Arg Gly Lys Lys Ala Asp Glu Leu Glu Arg Ile
GGGAGATGGGCGCGAGAAACTCCGTCTTGAGAGGGAAAAAAGCAGATGAATTAGAAAGAA
         .         .         .         .         .        600

Arg Leu Arg Pro Gly Gly Lys Lys Lys Tyr Arg Leu Lys His Ile Val Trp Ala Ala Asn
TCAGGTTACGGCCCGGCGGAAAGAAAAAGTACAGGCTAAAACATATTGTGTGGGCAGCGA
         .         .         .         .         .         .

Lys Leu Asp Arg Phe Gly Leu Ala Glu Ser Leu Leu Glu Ser Lys Glu Gly Cys Gln Lys
ATAAATTGGACAGATTCGGATTAGCAGAGAGCCTGTTGGAGTCAAAAGAGGGTTGTCAAA
         .         .         .        700        .         .

Ile Leu Thr Val Leu Asp Pro Met Val Pro Thr Gly Ser Glu Asn Leu Lys Ser Leu Phe
AAATTCTTACAGTTTTAGATCCAATGGTACCGACAGGTTCAGAAAATTTAAAAAGTCTTT
         .         .         .         .         .         .

Asn Thr Val Cys Val Ile Trp Cys Ile His Ala Glu Glu Lys Val Lys Asp Thr Glu Gly
TTAATACTGTCTGCGTCATTTGGTGCATACACGCAGAAGAGAAAGTGAAAGATACTGAAG
         .        800        .         .         .         .

Ala Lys Gln Ile Val Arg Arg His Leu Val Ala Glu Thr Gly Thr Ala Glu Lys Met Pro
GAGCAAAACAAATAGTGCGGAGACATCTAGTGGCAGAAACAGGAACTGCAGAGAAAATGC
         .         .         .         .         .        900

Ser Thr Ser Arg Pro Thr Ala Pro Ser Ser Glu Lys Gly Gly Asn Tyr Pro Val Gln His
CAAGCACAAGTAGACCAACAGCACCATCTAGCGAGAAGGGAGGAAATTACCCAGTGCAAC
         .         .         .         .         .         .

Val Gly Gly Asn Tyr Thr His Ile Pro Leu Ser Pro Arg Thr Leu Asn Ala Trp Val Lys
ATGTAGGCGGCAACTACACCCATATACCGCTGAGTCCCCGAACCCTAAATGCCTGGGTAA
         .         .         .       1000        .         .

Leu Val Glu Glu Lys Lys Phe Gly Ala Glu Val Val Pro Gly Phe Gln Ala Leu Ser Glu
AATTAGTAGAGGAAAAAAAGTTCGGGGCAGAAGTAGTGCCAGGATTTCAGGCACTCTCAG
         .         .         .         .         .         .

Gly Cys Thr Pro Tyr Asp Ile Asn Gln Met Leu Asn Cys Val Gly Asp His Gln Ala Ala
AAGGCTGCACGCCCTATGATATCAACCAAATGCTTAATTGTGTGGGCGACCATCAAGCAG
         .       1100        .         .         .         .

Met Gln Ile Ile Arg Glu Ile Ile Asn Glu Glu Ala Ala Glu Trp Asp Val Gln His Pro
CCATGCAGATAATCAGGGAGATTATCAATGAGGAAGCAGCAGAATGGGATGTGCAACATC
         .         .         .         .         .       1200
```

-continued

```
 Ile  Pro Gly Pro eu  Pro Ala Gly Gln Leu Arg Glu Pro Arg Gly Ser Asp Ile  Ala Gly
CAATACCAGGCCCCTTACCAGCGGGGCAGCTTAGAGAGCCAAGGGGATCTGACATAGCAG

 Thr Thr Ser Thr Val Glu Glu Gln Ile  Gln Trp Met Phe Arg Pro Gln Asn Pro Val Pro
GGACAACAAGCACAGTAGAAGAACAGATCCAGTGGATGTTTAGGCCACAAAATCCTGTAC
                                  1300

 Val Gly Asn Ile  Tyr Arg Arg Trp Ile  Gln Ile  Gly Leu Gln Lys Cys Val Arg Met Tyr
CAGTAGGAAACATCTATAGAAGATGGATCCAGATAGGATTGCAGAAGTGTGTCAGGATGT

 Asn Pro Thr Asn Ile  Leu Asp Ile  Lys Gln Gly Pro Lys Glu Pro Phe Gln Ser Tyr Val
ACAACCCGACCAACATCCTAGACATAAAACAGGGACCAAAGGAGCCGTTCCAAAGCTATG
          1400

 Asp Arg Phe Tyr Lys Ser Leu Arg Ala Glu Gln Thr Asp Pro Ala Val Lys Asn Trp Met
TAGATAGATTCTACAAAAGCTTGAGGGCAGAACAAACAGATCCAGCAGTGAAGAATTGGA
                                                        1500

 Thr Gln Thr Leu Leu Val Gln Asn Ala Asn Pro Asp Cys Lys Leu Val Leu Lys Gly Leu
TGACCCAAACACTGCTAGTACAAAATGCCAACCCAGACTGTAAATTAGTGCTAAAAGGAC

 Gly Met Asn Pro Thr Leu Glu Glu Met Leu Thr Ala Cys Gln Gly Val Gly Gly Pro Gly
TAGGGATGAACCCTACCTTAGAAGAGATGCTGACCGCCTGTCAGGGGGTAGGTGGGCCAG
                                  1600

 Gln Lys Ala Arg Leu Met Ala Glu Ala Leu Lys Glu Val Ile  Gly Pro Ala Pro Ile  Pro
GCCAGAAAGCTAGATTAATGGCAGAGGCCCTGAAAGAGGTCATAGGACCTGCCCCTATCC

 Phe Ala Ala Ala Gln Gln Arg Lys Ala Phe Lys Cys Trp Asn Cys Gly Lys Glu Gly His
CATTCGCAGCAGCCCAGCAGAGAAAGGCATTTAAATGCTGGAACTGTGGAAAGGAAGGGC
          1700

 Ser Ala Arg Gln Cys Arg Ala Pro Arg Arg Gln Gly Cys Trp Lys Cys Gly Lys Pro Gly
ACTCGGCAAGACAATGCCGAGCACCTAGAAGGCAGGGCTGCTGGAAGTGTGGTAAGCCAG
                                                        1800

                               Thr Gly Arg Phe Phe Arg Thr Gly Pro Leu Gly
 His Ile  Met Thr Asn Cys Pro Asp Arg Gln Ala Gly Phe Leu Gly Leu Gly Pro Trp Gly
GACACATCATGACAAACTGCCCAGATAGACAGGCAGGTTTTTTAGGACTGGGCCCTTGGG

 Lys Glu Ala Pro Gln Leu Pro Arg Gly Pro Ser Ser Ala Gly Ala Asp Thr Asn Ser Thr
  Lys Lys Pro Arg Asn Phe Pro Val Ala Gln Val Pro Gln Gly Leu Thr Pro Thr Ala Pro
GAAAGAAGCCCCGCAACTTCCCCGTGGCCCAAGTTCCGCAGGGGCTGACACCAACAGCAC
                                  1900

 Pro Ser Gly Ser Ser Ser Gly Ser Thr Gly Glu Ile  Tyr Ala Ala Arg Glu Lys Thr Glu
  Pro Val Asp Pro Ala Val Asp Leu Leu Glu Lys Tyr Met Gln Gln Gly Lys Arg Gln Arg
CCCCAGTGGATCCAGCAGTGGATCTACTGGAGAAATATATGCAGCAAGGGAAAAGACAGA

 Arg Ala Glu Arg Glu Thr Ile  Gln Gly Ser Asp Arg Gly Leu Thr Ala Pro Arg Ala Gly
  Glu Gln Arg Glu Arg Pro Tyr Lys Glu Val Thr Glu Asp Leu Leu His Leu Glu Gln Gly
GAGAGCAGAGAGAGAGACCATACAAGGAAGTGACAGAGGACTTACTGCACCTCGAGCAGG
          2000

 Gly Asp Thr Ile  Gln Gly Ala Thr Asn Arg Gly Leu Ala Ala Pro Gln Phe Ser Leu Trp
  Glu Thr Pro Tyr Arg Glu Pro Pro Thr Glu Asp Leu Leu His Leu Asn Ser Leu Phe Gly
GGGAGACACCATACAGGGAGCCACCAACAGAGGACTTGCTGCACCTCAATTCTCTCTTTG
                                                        2100

 Lys Arg Pro Val Val Thr Ala Tyr Ile  Glu Gly Gln Pro Val Glu Val Leu Leu Asp Thr
  Lys Asp Gln
GAAAAGACCAGTAGTCACAGCATACATTGAGGGTCAGCCAGTAGAAGTCTTGTTAGACAC

 Gly Ala Asp Asp Ser Ile  Val Ala Gly Ile  Glu Leu Gly Asn Asn Tyr Ser Pro Lys Ile
AGGGGCTGACGACTCAATAGTAGCAGGAATAGAGTTAGGGAACAATTATAGCCCAAAAAT
                                  2200

 Val Gly Gly Ile  Gly Gly Phe Ile  Asn Thr Lys Glu Tyr Lys Asn Val Glu Ile  Glu Val
AGTAGGGGGAATAGGGGGATTCATAAATACCAAGGAATATAAAAATGTAGAAATAGAAGT

 Leu Asn Lys Lys Val Arg Ala Thr Ile  Met Thr Gly Asp Thr Pro Ile  Asn Ile  Phe Gly
TCTAAATAAAAAGGTACGGGCCACCATAATGACAGGCGACACCCCAATCAACATTTTTGG
          2300
```

-continued

Arg Asn Ile Leu Thr Ala Leu Gly Met Ser Leu Asn Leu Pro Val Ala Lys Val Glu Pro
CAGAAATATTCTGACAGCCTTAGGCATGTCATTAAATCTACCAGTCGCCAAAGTAGAGCC
2400

Ile Lys Ile Met Leu Lys Pro Gly Lys Asp Gly Pro Lys Leu Arg Gln Trp Pro Leu Thr
AATAAAAATAATGCTAAAGCCAGGGAAAGATGGACCAAAACTGAGACAATGGCCCTTAAC

Lys Glu Lys Ile Glu Ala Leu Lys Glu Ile Cys Glu Lys Met Glu Lys Glu Gly Gln Leu
AAAAGAAAAAATAGAAGCACTAAAAGAAATCTGTGAAAAAATGGAAAAAGAAGGCCAGCT
2500

Glu Glu Ala Pro Pro Thr Asn Pro Tyr Asn Thr Pro Thr Phe Ala Ile Lys Lys Lys Asp
AGAGGAAGCACCTCCAACTAATCCTTATAATACCCCCACATTTGCAATCAAGAAAAAGGA

Lys Asn Lys Trp Arg Met Leu Ile Asp Phe Arg Glu Leu Asn Lys Val Thr Gln Asp Phe
CAAAAACAAATGGAGGATGCTAATAGATTTCAGAGAACTAAACAAGGTAACTCAAGATTT
2600

Thr Glu Ile Gln Leu Gly Ile Pro His Pro Ala Gly Leu Ala Lys Lys Arg Arg Ile Thr
CACAGAAATTCAGTTAGGAATTCCACACCCAGCAGGGTTGGCCAAGAAGAGAAGAATTAC
2700

Val Leu Asp Val Gly Asp Ala Tyr Phe Ser Ile Pro Leu His Glu Asp Phe Arg Pro Tyr
TGTACTAGATGTAGGGGATGCTTACTTTTCCATACCACTACATGAGGACTTTAGACCATA

Thr Ala Phe Thr Leu Pro Ser Val Asn Asn Ala Glu Pro Gly Lys Arg Tyr Ile Tyr Lys
TACTGCATTTACTCTACCATCAGTGAACAATGCAGAACCAGGAAAAAGATACATATATAA
2800

Val Leu Pro Gln Gly Trp Lys Gly Ser Pro Ala Ile Phe Gln His Thr Met Arg Gln Val
AGTCTTGCCACAGGGATGGAAGGGATCACCAGCAATTTTTCAACACACAATGAGACAGGT

Leu Glu Pro Phe Arg Lys Ala Asn Lys Asp Val Ile Ile Ile Gln Tyr Met Asp Asp Ile
ATTAGAACCATTCAGAAAAGCAAACAAGGATGTCATTATCATTCAGTACATGGATGATAT
2900

Leu Ile Ala Ser Asp Arg Thr Asp Leu Glu His Asp Arg Val Val Leu Gln Leu Lys Glu
CTTAATAGCTAGTGACAGGACAGATTTAGAACATGATAGGGTAGTCCTGCAGCTCAAGGA
3000

Leu Leu Asn Gly Leu Gly Phe Ser Thr Pro Asp Glu Lys Phe Gln Lys Asp Pro Pro Tyr
ACTTCTAAATGGCCTAGGATTTTCTACCCCAGATGAGAAGTTCCAAAAAGACCCTCCATA

His Trp Met Gly Tyr Glu Leu Trp Pro Thr Lys Trp Lys Leu Gln Lys Ile Gln Leu Pro
CCACTGGATGGGCTATGAACTATGGCCAACTAAATGGAAGTTGCAGAAAATACAGTTGCC
3100

Gln Lys Glu Ile Trp Thr Val Asn Asp Ile Gln Lys Leu Val Gly Val Leu Asn Trp Ala
CCAAAAAGAAATATGGACAGTCAATGACATCCAGAAGCTAGTGGGTGTCCTAAATTGGGC

Ala Gln Leu Tyr Pro Gly Ile Lys Thr Lys His Leu Cys Arg Leu Ile Arg Gly Lys Met
AGCACAACTCTACCCAGGGATAAAGACCAAACACTTATGTAGGTTAATCAGAGGAAAAAT
3200

Thr Leu Thr Glu Glu Val Gln Trp Thr Glu Leu Ala Glu Ala Glu Leu Glu Glu Asn Arg
GACACTCACAGAAGAAGTACAGTGGACAGAATTAGCAGAAGCAGAGCTAGAAGAAAACAG
3300

Ile Ile Leu Ser Gln Glu Gln Glu Gly His Tyr Tyr Gln Glu Glu Lys Glu Leu Glu Ala
AATTATCCTAAGCCAGGAACAAGAGGGACACTATTACCAAGAAGAAAAAGAGCTAGAAGC

Thr Val Gln Lys Asp Gln Glu Asn Gln Trp Thr Tyr Lys Ile His Gln Glu Glu Lys Ile
AACAGTCCAAAAGGATCAAGAGAATCAGTGGACATATAAAATACACCAGGAAGAAAAAAT
3400

Leu Lys Val Gly Lys Tyr Ala Lys Val Lys Asn Thr His Thr Asn Gly Ile Arg Leu Leu
TCTAAAAGTAGGAAAATATGCAAAGGTGAAAAACACCCATACCAATGGAATCAGATTGTT

Ala Gln Val Val Gln Lys Ile Gly Lys Glu Ala Leu Val Ile Trp Gly Arg Ile Pro Lys
AGCACAGGTAGTTCAGAAAATAGGAAAAGAAGCACTAGTCATTTGGGGACGAATACCAAA
3500

-continued

Phe His Leu Pro Val Glu Arg Glu Ile Trp Glu Gln Trp Trp Asp Asn Tyr Trp Gln Val
ATTTCACCTACCAGTAGAGAGAGAAATCTGGGAGCAGTGGTGGGATAACTACTGGCAAGT
3600

Thr Trp Ile Pro Asp Trp Asp Phe Val Ser Thr Pro Pro Leu Val Arg Leu Ala Phe Asn
GACATGGATCCCAGACTGGGACTTCGTGTCTACCCCACCACTGGTCAGGTTAGCGTTTAA

Leu Val Gly Asp Pro Ile Pro Gly Ala Glu Thr Phe Tyr Thr Asp Gly Ser Cys Asn Arg
CCTGGTAGGGGATCCTATACCAGGTGCAGAGACCTTCTACACAGATGGATCCTGCAATAG
3700

Gln Ser Lys Glu Gly Lys Ala Gly Tyr Val Thr Asp Arg Gly Lys Asp Lys Val Lys Lys
GCAATCAAAAGAAGGAAAAGCAGGATATGTAACAGATAGAGGGAAAGACAAGGTAAAGAA

Leu Glu Gln Thr Thr Asn Gln Gln Ala Glu Leu Glu Ala Phe Ala Met Ala Leu Thr Asp
ACTAGAGCAAACTACCAATCAGCAAGCAGAACTAGAAGCCTTTGCGATGGCACTAACAGA
3800

Ser Gly Pro Lys Val Asn Ile Ile Val Asp Ser Gln Tyr Val Met Gly Ile Ser Ala Ser
CTCGGGTCCAAAAGTTAATATTATAGTAGACTCACAGTATGTAATGGGGATCAGTGCAAG
3900

Gln Pro Thr Glu Ser Glu Ser Lys Ile Val Asn Gln Ile Ile Glu Glu Met Ile Lys Lys
CCAACCAACAGAGTCAGAAAGTAAAATAGTGAACCAGATCATAGAAGAAATGATAAAAAA

Glu Ala Ile Tyr Val Ala Trp Val Pro Ala His Lys Gly Ile Gly Gly Asn Gln Glu Val
GGAAGCAATCTATGTTGCATGGGTCCCAGCCCACAAAGGCATAGGGGGAAACCAGGAAGT
4000

Asp His Leu Val Ser Gln Gly Ile Arg Gln Val Leu Phe Leu Glu Lys Ile Glu Pro Ala
AGATCATTTAGTGAGTCAGGGTATCAGACAAGTGTTGTTCCTGGAAAAAATAGAGCCCGC

Gln Glu Glu His Glu Lys Tyr His Ser Asn Val Lys Glu Leu Ser His Lys Phe Gly Ile
TCAGGAAGAACATGAAAAATATCATAGCAATGTAAAAGAACTGTCTCATAAATTTGGAAT
4100

Pro Asn Leu Val Ala Arg Gln Ile Val Asn Ser Cys Ala Gln Cys Gln Gln Lys Gly Glu
ACCCAATTTAGTGGCAAGGCAAATAGTAAACTCATGTGCCCAATGTCAACAGAAAGGGGA
4200

Ala Ile His Gly Gln Val Asn Ala Glu Leu Gly Thr Trp Gln Met Asp Cys Thr His Leu
AGCTATACATGGGCAAGTAAATGCAGAACTAGGCACTTGGCAAATGGACTGCACACATTT

Glu Gly Lys Ile Ile Ile Val Ala Val His Val Ala Ser Gly Phe Ile Glu Ala Glu Val
AGAAGGAAAGATCATTATAGTAGCAGTACATGTTGCAAGTGGATTTATAGAAGCAGAAGT
4300

Ile Pro Gln Glu Ser Gly Arg Gln Thr Ala Leu Phe Leu Leu Lys Leu Ala Ser Arg Trp
CATCCCACAGGAATCAGGAAGACAAACAGCACTCTTCCTATTGAAACTGGCAAGTAGGTG

Pro Ile Thr His Leu His Thr Asp Asn Gly Ala Asn Phe Thr Ser Gln Glu Val Lys Met
GCCAATAACACACTTGCATACAGATAATGGTGCCAACTTCACTTCACAGGAGGTGAAGAT
4400

Val Ala Trp Trp Ile Gly Ile Glu Gln Ser Phe Gly Val Pro Tyr Asn Pro Gln Ser Gln
GGTAGCATGGTGGATAGGTATAGAACAATCCTTTGGAGTACCTTACAATCCACAGAGCCA
4500

Gly Val Val Glu Ala Met Asn His His Leu Lys Asn Gln Ile Ser Arg Ile Arg Glu Gln
AGGAGTAGTAGAAGCAATGAATCACCATCTAAAAAACCAAATAAGTAGAATCAGAGAACA

Ala Asn Thr Ile Glu Thr Ile Val Leu Met Ala Ile His Vys Met Asn Phe Lys Arg Arg
GGCAAATACAATAGAAACAATAGTACTAATGGCAATTCATTGCATGAATTTTAAAAGAAG
4600

Gly Gly Ile Gly Asp Met Thr Pro Ser Glu Arg Leu Ile Asn Met Ile Thr Thr Glu Gln
GGGGGGAATAGGGGATATGACTCCATCAGAAAGATTAATCAATATGATCACCACAGAACA

Glu Ile Gln Phe Leu Gln Ala Lys Asn Ser Lys Leu Lys Asp Phe Arg Val Tyr Phe Arg
AGAGATACAATTCCTCCAAGCCAAAAATTCAAAATTAAAAGATTTTCGGGTCTATTTCAG
4700

-continued

Glu Gly Arg Asp Gln Leu Trp Lys Gly Pro Gly Glu Leu Leu Trp Lys Gly Glu Gly Ala
AGAAGGCAGAGATCAGTTGTGGAAAGGACCTGGGGAACTACTGTGGAAAGGAGAAGGAGC
4800

Val Leu Val Lys Val Gly Thr Asp Ile Lys Ile Ile Pro Arg Arg Lys Ala Lys Ile Ile
AGTCCTAGTCAAGGTAGGAACAGACATAAAAATAATACCAAGAAGGAAAGCCAAGATCCT

Arg Asp Tyr Gly Gly Arg Gln Glu Met Asp Ser Gly Ser His Leu Glu Gly Ala Arg Glu
Met Glu Glu Asp Lys Arg Trp Ile Val Val Pro Thr Trp Arg Val Pro Gly Arg
CAGAGACTATGGAGGAAGACAAGAGATGGATAGTGGTTCCCACCTGGAGGGTGCCAGGGA
4900

Asp Gly Glu Met Ala
Met Glu Lys Trp His Ser Leu Val Lys Tyr Leu Lys Tyr Lys Thr Lys Asp Leu Glu Lys
GGATGGAGAAATGGCATAGCCTTGTCAAGTATCTAAAATACAAAACAAAGGATCTAGAAA

Val Cys Tyr Val Pro His His Lys Val Gly Trp Ala Trp Trp Thr Cys Ser Arg Val Ile
AGGTGTGCTATGTTCCCCACCATAAGGTGGGATGGGCATGGTGGACTTGCAGCAGGGTAA
5000

Phe Pro Leu Lys Gly Asn Ser His Leu Glu Ile Gln Ala Tyr Trp Asn Leu Thr Pro Glu
TATTCCCATTAAAAGGAAACAGTCATCTAGAGATACAGGCATATTGGAACTTAACACCAG
5100

Lys Gly Trp Leu Ser Ser Tyr Ser Val Arg Ile Thr Trp Tyr Thr Glu Lys Phe Trp Thr
AAAAAGGATGGCTCTCCTCTTATTCAGTAAGAATAACTTGGTACACAGAAAAGTTCTGGA

Asp Val Thr Pro Asp Cys Ala Asp Val Leu Ile His Ser Thr Tyr Phe Pro Cys Phe Thr
CAGATGTTACCCCAGACTGTGCAGATGTCCTAATACATAGCACTTATTTCCCTTGCTTTA
5200

Ala Gly Glu Val Arg Arg Ala Ile Arg Gly Glu Lys Leu Leu Ser Cys Cys Asn Tyr Pro
CAGCAGGTGAAGTAAGAAGAGCCATCAGAGGGGAAAAGTTATTGTCCTGCTGCAATTATC

Arg Ala His Arg Ala Gln Val Pro Ser Leu Gln Phe Leu Ala Leu Val Val Val Gln Gln
CCCGAGCTCATAGAGCCCAGGTACCGTCACTTCAATTTCTGGCCTTAGTGGTAGTGCAAC
5300

Met Thr Asp Pro Arg Glu Thr Val Pro Pro Gly Asn Ser Gly Glu Glu Thr Ile Gly
Asn Asp Arg Pro Gln Arg Asp Ser Thr Thr Arg Lys Gln Arg Arg Arg Asp Tyr Arg Arg
AAAATGACAGACCCCAGAGAGACAGTACCACCAGGAAACAGCGGCGAAGAGACTATCGGA
5400

Glu Ala Phe Ala Trp Leu Asn Arg Thr Val Glu Ala Ile Asn Arg Glu Ala Val Asn His
Gly Leu Arg Leu Ala Lys Gln Asp Ser Arg Ser His Lys Gln Arg Ser Ser Glu Ser Pro
GAGGCCTTCGCCTGGCTAAACAGGACAGTAGAAGCCATAAACAGAGAAGCAGTGAATCAC

Leu Pro Arg Glu Leu Ile Phe Gln Val Trp Gln Arg Ser Trp Arg Tyr Trp His Asp Glu
Thr Pro Arg Thr Tyr Phe Pro Gly Val Ala Glu Val Leu Glu Ile Leu Ala
CTACCCCGAGAACTTATTTTCCAGGTGTGGCAGAGGTCCTGGAGATACTGGCATGATGAA
5500

Gln Gly Met Ser Glu Ser Tyr Thr Lys Tyr Arg Tyr Leu Cys Ile Ile Gln Lys Ala Val
CAAGGGATGTCAGAAAGTTACACAAAGTATAGATATTTGTGCATAATACAGAAAGCAGTG

Tyr Met His Val Arg Lys Gly Cys Thr Cys Leu Gly Arg Gly His Gly Pro Gly Gly Trp
TACATGCATGTTAGGAAAGGGTGTACTTGCCTGGGGAGGGGACATGGGCCAGGAGGGTGG
5600

Arg Pro Gly Pro Pro Pro Pro Pro Pro Pro Gly Leu Val
Met Ala Glu Ala Pro Thr Glu
AGACCAGGGCCTCCTCCTCCTCCCCCTCCAGGTCTGGTCTAATGGCTGAAGCACCAACAG
5700

Leu Pro Pro Val Asp Gly Thr Pro Leu Arg Glu Pro Gly Asp Glu Trp Ile Ile Glu Ile
AGCTCCCCCCGGTGGATGGGACCCCACTGAGGGAGCCAGGGGATGAGTGGATAATAGAAA

Leu Arg Glu Ile Lys Glu Glu Ala Leu Lys His Phe Asp Pro Arg Leu Leu Ile Ala Leu
TCTTGAGAGAAATAAAAGAAGAAGCTTTAAAGCATTTTGACCCTCGCTTGCTAATTGCTC
5800

Met Glu Thr Phe Leu Lys Ala Pro Glu Ser Ser Leu
Gly Lys Tyr Ile Tyr Thr Arg His Gly Asp Thr Leu Glu Gly Ala Arg Glu Leu Ile Lys
TTGGCAAATATATCTATACTAGACATGGAGACACCCTTGAAGGCGCCAGAGAGCTCATTA

-continued

Lys Ser Cys Asn Glu Pro Phe Ser Arg Thr Ser Glu Gln Asp Val Ala Thr Gln Glu Leu
Val Leu Gln Arg Ala Leu Phe Thr His Phe Arg Ala Gly Cys Gly His Ser Arg Ile Gly
AAGTCCTGCAACGAGCCCTTTTCACGCACTTCAGAGCAGGATGTGGCCACTCAAGAATTG
5900

Ala Arg Gln Gly Glu Glu Ile Leu Ser Gln Leu Tyr Arg Pro Leu Glu Thr Cys Asn Asn
Gln Thr Arg Gly Gly Asn Pro Leu Ser Ala Ile Pro Thr Pro Arg Asn Met Gln
GCCAGACAAGGGGAGGAAATCCTCTCTCAGCTATACCGACCCCTAGAAACATGCAATAAC
6000

Ser Cys Tyr Cys Lys Arg Cys Cys Tyr His Cys Gln Met Cys Phe Leu Asn Lys Gly Leu
TCATGCTATTGTAAGCGATGCTGCTACCATTGTCAGATGTGTTTTCTAAACAAGGGGCTC

Gly Ile Cys Tyr Glu Arg Lys Gly Arg Arg Arg Arg Thr Pro Lys Lys Thr Lys Thr His
Met Asn Glu Arg Ala Asp Glu Glu Gly Leu Gln Arg Lys Leu Arg Leu Ile
GGGATATGTTATGAACGAAAGGGCAGACGAAGAAGGACTCCAAAGAAAACTAAGACTCAT
6100

Pro Ser Pro Thr Pro Asp Lys
Arg Leu Leu His Gln Thr
Met Met Asn Gln Leu Leu Ile Ala Ile Leu Leu Ala
CCGTCTCCTACACCAGCACAAGTGAGTATGATGAATCAGCTGCTTATTGCCATTTTATTAG

Ser Ala Cys Leu Val Tyr Cys Thr Gln Tyr Val Thr Val Phe Tyr Gly Val Pro Thr Trp
CTAGTGCTTGCTTAGTATATTGCACCCAATATGTAACTGTTTTCTATGGCGTACCCACGT
6200

Lys Asn Ala Thr Thr Pro Leu Phe Cys Ala Thr Arg Asn Arg Asp Thr Trp Gly Thr Ile
GGAAAAATGCAACCATTCCCCTCTTTTGTGCAACCAGAAATAGGGATACTTGGGGAACCA
6300

Gln Cys Leu Pro Asp Asn Asp Asp Tyr Gln Glu Ile Thr Leu Asn Val Thr Glu Ala Phe
TACAGTGCTTGCCTGACAATGATGATTATCAGGAAATAACTTTGAATGTAACAGAGGCTT

Asp Ala Trp Asn Asn Thr Val Thr Glu Gln Ala Ile Glu Asp Val Trp His Leu Phe Glu
TTGATGCATGGAATAATACAGTAACAGAACAAGCAATAGAAGATGTCTGGCATCTATTCG
6400

Thr Ser Ile Lys Pro Cys Val Lys Leu Thr Pro Leu Cys Val Ala Met Lys Cys Ser Ser
AGACATCAATAAAACCATGTGTCAAACTAACACCTTTATGTGTAGCAATGAAATGCAGCA

Thr Glu Ser Ser Thr Gly Asn Asn Thr Thr Ser Lys Ser Thr Ser Thr Thr Thr Thr Thr
GCACAGAGAGCAGCACAGGGAACAACACAACCTCAAAGAGCACAAGCACAACCACAACCA
6500

Pro Thr Asp Gln Glu Gln Glu Ile Ser Glu Asp Thr Pro Cys Ala Arg Ala Asp Asn Cys
CACCCACAGACCAGGAGCAAGAGATAAGTGAGGATACTCCATGCGCACGCGCAGACAACT
6600

Ser Gly Leu Gly Glu Glu Glu Thr Ile Asn Cys Gln Phe Asn Met Thr Gly Leu Glu Arg
GCTCAGGATTGGGAGAGGAAGAAACGATCAATTGCCAGTTCAATATGACAGGATTAGAAA

Asp Lys Lys Lys Gln Tyr Asn Glu Thr Trp Tyr Ser Lys Asp Val Val Cys Glu Thr Asn
GAGATAAGAAAAAACAGTATAATGAAACATGGTACTCAAAAGATGTGGTTTGTGAGACAA
6700

Asn Ser Thr Asn Gln Thr Gln Cys Tyr Met Asn His Cys Asn Thr Ser Val Ile Thr Glu
ATAATAGCACAAATCAGACCCAGTGTTACATGAACCATTGCAACACATCAGTCATCACAG

Ser Cys Asp Lys His Tyr Trp Asp Ala Ile Arg Phe Arg Tyr Cys Ala Pro Pro Gly Tyr
AATCATGTGACAAGCACTATTGGGATGCTATAAGGTTTAGATACTGTGCACCACCGGGTT
6800

Ala Leu Leu Arg Cys Asn Asp Thr Asn Tyr Ser Gly Phe Ala Pro Asn Cys Ser Lys Val
ATGCCCTATTAAGATGTAATGATACCAATTATTCAGGCTTTGCACCCAACTGTTCTAAAG
6900

Val Ala Ser Thr Cys Thr Arg Met Met Glu Thr Gln Thr Ser Thr Trp Phe Gly Phe Asn
TAGTAGCTTCTACATGCACCAGGATGATGGAAACGCAAACTTCCACATGGTTTGGCTTTA

Gly Thr Arg Ala Glu Asn Arg Thr Tyr Ile Tyr Trp His Gly Arg Asp Asn Arg Thr Ile
ATGGCACTAGAGCAGAGAATAGAACATATATCTATTGGCATGGCAGAGATAATAGAACTA
7000

-continued

Ile Ser Leu Asn Lys Tyr Tyr Asn Leu Ser Leu His Cys Lys Arg Pro Gly Asn Lys Thr
TCATCAGCTTAAACAAATATTATAATCTCAGTTTGCATTGTAAGAGGCCAGGGAATAAGA

Val Lys Gln Ile Met Leu Met Ser Gly His Val Phe His Ser His Tyr Gln Pro Ile Asn
CAGTGAAACAAATAATGCTTATGTCAGGACATGTGTTTCACTCCCACTACCAGCCGATCA
7100

Lys Arg Pro Arg Gln Ala Trp Cys Trp Phe Lys Gly Lys Trp Lys Asp Ala Met Gln Glu
ATAAAAGACCCAGACAAGCATGGTGCTGGTTCAAAGGCAAATGGAAAGACGCCATGCAGG
7200

Val Lys Glu Thr Leu Ala Lys His Pro Arg Tyr Arg Gly Thr Asn Asp Thr Arg Asn Ile
AGGTGAAGGAAACCCTTGCAAAACATCCCAGGTATAGAGGAACCAATGACACAAGGAATA

Ser Phe Ala Ala Pro Gly Lys Gly Ser Asp Pro Glu Val Ala Tyr Met Trp Thr Asn Cys
TTAGCTTTGCAGCGCCAGGAAAAGGCTCAGACCCAGAAGTAGCATACATGTGGACTAACT
7300

Arg Gly Glu Phe Leu Tyr Cys Asn Met Thr Trp Phe Leu Asn Trp Ile Glu Asn Lys Thr
GCAGAGGAGAGTTTCTCTACTGCAACATGACTTGGTTCCTCAATTGGATAGAGAATAAGA

His Arg Asn Tyr Ala Pro Cys His Ile Lys Gln Ile Ile Asn Thr Trp His Lys Val Gly
CACACCGCAATTATGCACCGTGCCATATAAAGCAAATAATTAACACATGGCATAAGGTAG
7400

Arg Asn Val Tyr Leu Pro Pro Arg Glu Gly Glu Leu Ser Cys Asn Ser Thr Val Thr Ser
GGAGAAATGTATATTTGCCTCCCAGGGAAGGGGAGCTGTCCTGCAACTCAACAGTAACCA
7500

Ile Ile Ala Asn Ile Asp Trp Gln Asn Asn Asn Gln Thr Asn Ile Thr Phe Ser Ala Glu
GCATAATTGCTAACATTGACTGGCAAAACAATAATCAGACAAACATTACCTTTAGTGCAG

Val Ala Glu Leu Tyr Arg Leu Glu Leu Gly Asp Tyr Lys Leu Val Glu Ile Thr Pro Ile
AGGTGGCAGAACTATACAGATTGGAGTTGGGAGATTATAAATTGGTAGAAATAACACCAA
7600

Gly Phe Ala Pro Thr Lys Glu Lys Arg Tyr Ser Ser Ala His Gly Arg His Thr Arg Gly
TTGGCTTCGCACCTACAAAAGAAAAAAGATACTCCTCTGCTCACGGGAGACATACAAGAG

Val Phe Val Leu Gly Phe Leu Gly Phe Leu Ala Thr Ala Gly Ser Ala Met Gly Ala Ala
GTGTGTTCGTGCTAGGGTTCTTGGGTTTTCTCGCAACAGCAGGTTCTGCAATGGGCGCGG
7700

Ser Leu Thr Val Ser Ala Gln Ser Arg Thr Leu Leu Ala Gly Ile Val Gln Gln Gln Gln
CGTCCCTGACCGTGTCGGCTCAGTCCCGGACTTTACTGGCCGGGATAGTGCAGCAACAGC
7800

Gln Leu Leu Asp Val Val Lys Arg Gln Gln Glu Leu Leu Arg Leu Thr Val Trp Gly Thr
AACAGCTGTTGGACGTGGTCAAGAGACAACAAGAACTGTTGCGACTGACCGTCTGGGGAA

Lys Asn Leu Gln Ala Arg Val Thr Ala Ile Glu Lys Tyr Leu Gln Asp Gln Ala Arg Leu
CGAAAAACCTCCAGGCAAGAGTCACTGCTATAGAGAAGTACCTACAGGACCAGGCGCGGC
7900

Asn Ser Trp Gly Cys Ala Phe Arg Gln Val Cys His Thr Thr Val Pro Trp Val Asn Asp
TAAATTCATGGGGATGTGCGTTTAGACAAGTCTGCCACACTACTGTACCATGGGTTAATG

Ser Leu Ala Pro Asp Trp Asp Asn Met Thr Trp Gln Glu Trp Glu Lys Gln Val Arg Tyr
ATTCCTTAGCACCTGACTGGGACAATATGACGTGGCAGGAATGGGAAAAACAAGTCCGCT
8000

Leu Glu Ala Asn Ile Ser Lys Ser Leu Glu Gln Ala Gln Ile Gln Gln Glu Lys Asn Met
ACCTGGAGGCAAATATCAGTAAAAGTTTAGAACAGGCACAAATTCAGCAAGAGAAAAATA
8100

Tyr Glu Leu Gln Lys Leu Asn Ser Trp Asp Ile Phe Gly Asn Trp Phe Asp Leu Thr Ser
TGTATGAACTACAAAAATTAAATAGCTGGGATATTTTTGGCAATTGGTTTGACTTAACCT

Trp Val Lys Tyr Ile Gln Tyr Gly Val Leu Ile Ile Val Ala Val Ile Ala Leu Arg Ile
CCTGGGTCAAGTATATTCAATATGGAGTGCTTATAATAGTAGCAGTAATAGCTTTAAGAA
8200

-continued

Val Ile Tyr Val Val Gln Met Leu Ser Arg Leu Arg Lys Gly Tyr Arg Pro Val Phe Ser
TAGTGATATATGTAGTACAAATGTTAAGTAGGCTTAGAAAGGGCTATAGGCCTGTTTTCT

Ser Ile Ser Thr Arg Thr Gly Asp Ser Gln Pro
Asn Pro Tyr Pro Gln Gly Pro Gly Thr Ala Ser Gln
Ser Pro Pro Gly Tyr Ile Gln Gln Ile His Ile His Lys Asp Arg Gly Gln Pro Ala Asn
CTTCCCCCCCCGGTTATATCCAACAGATCCATATCCACAAGGACCGGGGACAGCCAGCCA
8300

Thr Lys Lys Gln Lys Lys Thr Val Glu Ala Thr Val Glu Thr Asp Thr Gly Pro Gly Arg
Arg Arg Asn Arg Arg Arg Arg Trp Lys Gln Arg Trp Arg Gln Ile Leu Ala Leu Ala Asp
Glu Glu Thr Glu Glu Asp Gly Gly Ser Asn Gly Gly Asp Arg Tyr Trp Pro Trp Pro Ile
ACGAAGAAACAGAAGAAGACGGTGGAAGCAACGGTGGAGACAGATACTGGCCCTGGCCGA
8400

Ser Ile Tyr Thr Phe Pro Asp Pro Pro Ala Asp Ser Pro Leu Asp Gln Thr Ile Gln His
Ala Tyr Ile His Phe Leu Ile Arg Gln Leu Ile Arg Leu Leu Thr Arg Leu Tyr Ser Ile
TAGCATATATACATTTCCTGATCCGCCAGCTGATTCGCCTCTTGACCAGACTATACAGCA

Leu Gln Gly Leu Thr Ile Gln Glu Leu Pro Asp Pro Pro Thr His Leu Pro Glu Ser Gln
Cys Arg Asp Leu Leu Ser Arg Ser Phe Leu Thr Leu Gln Leu Ile Tyr Gln Asn Leu Arg
TCTGCAGGGACTTACTATCCAGGAGCTTCCTGACCCTCCAACTCATCTACCAGAATCTCA
8500

Arg Leu AlA Glu Thr Met Gly Ala Ser Gly Ser Lys Lys
Asp Trp Leu Arg Leu Arg Thr Ala Phe Leu Gln Tyr Gly Cys Glu Trp Ile Gln Glu Ala
GAGACTGGCTGAGACTTAGAACAGCCTTCTTGCAATATGGGTGCGAGTGGATCCAAGAAG

His Ser Arg Pro Pro Arg Gly Leu Gln Glu Arg Leu Leu Arg Ala Arg Ala Gly Ala Cys
Phe Gln Ala Ala Ala Arg Ala Thr Arg Glu Thr Leu Ala Gly Ala Cys Arg Gly Leu Trp
CATTCCAGGCCGCCGCGAGGGCTACAAGAGAGACTCTTGCGGGCGCGTGCAGGGGCTTGT
8600

Gly Gly Tyr Trp Asn Glu Ser Gly Gly Glu Tyr Ser Arg Phe Gln Glu Gly Ser Asp Arg
Arg Val Leu Glu Arg Ile Gly Arg Gly Ile Leu Ala Val Pro Arg Arg Ile Arg Gln Gly
GGAGGGTATTGGAACGAATCGGGAGGGGAATACTCGCGGTTCCAAGAAGGATCAGACAGG
8700

Glu Gln Lys Ser Pro Ser Cys Glu Gly Arg Gln Tyr Gln Gln Gly Asp Phe Met Asn Thr
Ala Glu Ile Ala Leu Leu
GAGCACAAATCGCCCTCCTGTGAGGGACGGCAGTATCAGCAGGGAGACTTTATGAATACT

Pro Trp Lys Asp Pro Ala Ala Glu Arg Glu Lys Asn Leu Tyr Arg Gln Gln Asn Met Asp
CCATGGAAGGACCCAGCAGCAGAAAGGGAGAAAAATTTGTACAGGCAACAAAATATGGAT
8800

Asp Val Asp Ser Asp Asp Asp Asp Gln Val Arg Val Ser Val Thr Pro Lys Val Pro Leu
GATGTAGATTCAGATGATGATGACCAAGTAAGAGTTTCTGTCACACCAAAAGTACCACTA

Arg Pro Met Thr His Arg Leu Ala Ile Asp Met Ser His Leu Ile Lys Thr Arg Gly Gly
AGACCAATGACACATAGATTGGCAATAGATATGTCACATTTAATAAAAACAAGGGGGGGA
8900

Leu Glu Gly Met Phe Tyr Ser Glu Arg Arg His Lys Ile Leu Asn Ile Tyr Leu Glu Lys
CTGGAAGGGATGTTTTACAGTGAAAGAAGACATAAAATCTTAAATATATACTTAGAAAAG
9000

Glu Glu Gly Ile Ile Ala Asp Trp Gln Asn Tyr Thr His Gly Pro Gly Val Arg Tyr Pro
GAAGAAGGGATAATTGCAGATTGGCAGAACTACACTCATGGGCCAGGAGTAAGATACCCA

Met Phe Phe Gly Trp Leu Trp Lys Leu Val Pro Val Asp Val Pro Gln Glu Gly Glu Asp
ATGTTCTTTGGGTGGCTATGGAAGCTAGTACCAGTAGATGTCCCACAAGAAGGGGAGGAC
9100

Thr Glu Thr His Cys Leu Val His Pro Ala Gln Thr Ser Lys Phe Asp Asp Pro His Gly
ACTGAGACTCACTGCTTAGTACATCCAGCACAAACAAGCAAGTTTGATGACCCGCATGGG

Glu Thr Leu Val Trp Glu Phe Asp Pro Leu Leu Ala Tyr Ser Tyr Glu Ala Phe Ile Arg
GAGACACTAGTCTGGGAGTTTGATCCCTTGCTGGCTTATAGTTACGAGGCTTTTATTCGG
9200

Tyr Pro Glu Glu Phe Gly His Lys Ser Gly Leu Pro Glu Glu Glu Trp Lys Ala Arg Leu
TACCCAGAGGAATTTGGGCACAAGTCAGGCCTGCCAGAGGAAGAGTGGAAGGCGAGACTG
9300

-continued

```
Lys Ala Arg Gly Ile Pro Phe Ser
AAAGCAAGAGGAATACCATTTAGTTAAAGACAGGAACAGCTATACTTGGTCAGGGCAGGA

AGTAACTAACAGAAACAGCTGAGACTGCAGGGACTTTCCAGAAGGGGCTGTAACCAAGGG
                                       9400

AGGGACATGGGAGGAGCTGGTGGGGAACGCCCTCATATTCTCTGTATAAATATACCCGCT

AGCTTGCATTGTACTTCGGTCGCTCTGCGGAGAGGCTGGCAGATTGAGCCCTGGGAGGTT
                9500

CTCTCCAGCAGTAGCAGGTAGAGCCTGGGTGTTCCCTGCTAGACTCTCACCAGCACTTGG
                                                          9600

CCGGTGCTGGGCAGACGGCCCCACGCTTGCTTGCTTAAAAACCTCCTTAATAAAGCTGCC

AGTTAGAAGCA
```

Example 5: Sequences of the Coding Regions for the Envelope Protein and GAG Product of the ROD HIV-2 Isolate Through experimental analysis of the HIV-2 ROD isolate, the following sequences were identified for the regions encoding the env and gag gene products. One of ordinary skill in the art will recognize that the numbering for both gene regions which follow begins for convenience with "1" rather than the corresponding number for its initial nucleotide as given in Example 4, above, in the context of the complete genomic sequence.

Envelope sequence

```
Met Met Asn Gln Leu Leu Ile Ala Ile Leu Leu Ala Ser Ala Cys
ATGATGAATCAGCTGCTTATTGCCATTTTATTAGCTAGTGCTTGC

Leu Val Tyr Cys Thr Gln Tyr Val Thr Val Phe Tyr Gly Val Pro
TTAGTATATTGCACCCAATATGTAACTGTTTTCTATGGCGTACCC

Thr Trp Lys Asn Ala Thr Ile Pro Leu Phe Cys Ala Thr Arg Asn
ACGTGGAAAAATGCAACCATTCCCCTGTTTTGTGCAACCAGAAAT
      100

Arg Asp Thr Trp Gly Thr Ile Gln Cys Leu Pro Asp Asn Asp Asp
AGGGATACTTGGGGAACCATACAGTGCTTGCCTGACAATGATGAT

Tyr Gln Glu Ile Thr Leu Asn Val Thr Glu Ala Phe Asp Ala Trp
TATCAGGAAATAACTTTGAATGTAACAGAGGCTTTTGATGCATGG
                 200

Asn Asn Thr Val Thr Glu Gln Ala Ile Glu Asp Val Trp His Leu
AATAATACAGTAACAGAACAAGCAATAGAAGATGTCTGGCATCTA

Phe Glu Thr Ser Ile Lys Pro Cys Val Lys Leu Thr Pro Leu Cys
TTCGAGACATCAATAAAACCATGTGTGAAACTAACACCTTTATGT
                                  300

Val Ala Met Lys Cys Ser Ser Thr Glu Ser Ser Thr Gly Asn Asn
GTAGCAATGAAATGCAGCAGCACAGAGAGCAGCACAGGGAACAAC

Thr Thr Ser Lys Ser Thr Ser Thr Thr Thr Thr Thr Pro Thr Asp
ACAACCTCAAAGAGCACAAGCACAACCACAACCACACCCAGAGAC
                                              400

Gln Glu Gln Glu Ile Ser Glu Asp Thr Pro Cys Ala Arg Ala Asp
CAGGAGCAAGAGATAAGTGAGGATACTCCATGCGCACGCGCAGAC

Asn Cys Ser Gly Leu Gly Glu Glu Glu Thr Ile Asn Cys Gln Phe
AACTGCTCAGGATTGGGAGAGGAAGAAACGATCAATTGCCAGTTC

Asn Met Thr Gly Leu Glu Arg Asp Lys Lys Lys Gln Tyr Asn Glu
AATATGACAGGATTAGAAAGAGATAAGAAAAAACAGTATAATGAA
  500
```

-continued

Envelope sequence

Thr Trp Tyr Ser Lys Asp Val Val Cys Glu Thr Asn Asn Ser Thr
ACATGGTACTCAAAAGATGTGGTTTGTGAGACAAATAATAGCACA

Asn Gln Thr Gln Cys Tyr Met Asn His Cys Asn Thr Ser Val Ile
AATCAGACCCAGTGTTACATGAACCATTGCAACACATCAGTCATC
600

Thr Glu Ser Cys Asp Lys His Tyr Trp Asp Ala Ile Arg Phe Arg
ACAGAATCATGTGACAAGCACTATTGGGATGCTATAAGGTTTAGA

Tyr Cys Ala Pro Pro Gly Tyr Ala Leu Leu Arg Cys Asn Asp Thr
TACTGTGCACCACCGGGTTATGCCCTATTAAGATGTAATGATACC
700

Asn Tyr Ser Gly Phe Ala Pro Asn Cys Ser Lys Val Val Ala Ser
AATTATTCAGGCTTTGCACCCAACTGTTCTAAAGTAGTAGCTTCT

Thr Cys Thr Arg Met Met Glu Thr Gln Thr Ser Thr Trp Phe Gly
ACATGCACCAGGATGATGGAAACGCAAACTTCCACATGGTTTGGC
800

Phe Asn Gly Thr Arg Ala Glu Asn Arg Thr Tyr Ile TyrTrp His
TTTAATGGCACTAGAGCAGAGAATAGAACATATATCTATTGGCAT

Gly Arg Asp Asn Arg Thr Ile Ile Ser Leu Asn Lys Tyr Tyr Asn
GGCAGAGATAATAGAACTATCATCAGCTTAAACAAATATTATAAT
900

Leu Ser Leu His Cys Lys Arg Pro Gly Asn Lys Thr Val Lys Gln
CTCAGTTTGCATTGTAAGAGGCCAGGGAATAAGACAGTGAAACAA

Ile Met Leu Met Ser Gly His Val Phe His Ser His Tyr Gln Pro
ATAATGCTTATGTCAGGACATGTGTTTCACTCCCACTACCAGCCG

Ile Asn Lys Arg Pro Arg Gln Ala Trp Cys Trp Phe Lys Gly Lys
ATCAATAAAAGACCCAGACAAGCATGGTGCTGGTTCAAAGGCAAA
1000

Trp Lys Asp Ala Met Gln Glu Val Lys Thr Leu Ala Lys His Pro
TGGAAAGACGCCATGCAGGAGGTGAAGACCCTTGCAAAACATCCC

Arg Tyr Arg Gly Thr Asn Asp Thr Arg Asn Ile Ser Phe Ala Ala
AGGTATAGAGGAACCAATGACACAAGGAATATTAGCTTTGCAGCG
1100

Pro Gly Lys Gly Ser Asp Pro Glu Val Ala Tyr Met Trp Thr Asn
CCAGGAAAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
1200

Trp Ile Glu Asn Lys Thr His Arg Asn Tyr Ala Pro Cys His Ile
TGGATAGAGAATAAGACACACCGCAATTATGCACCGTGCCATATA

Lys Gln Ile Ile Asn Thr Trp His Lys Val Gly Arg Asn Val Tyr
AAGCAAATAATTAACACATGGCATAAGGTAGGGAGAAATGTATAT
1300

Leu Pro Pro Arg Glu Gly Glu Leu Ser Cys Asn Ser Thr Val Thr
TTGCCTCCCAGGGAAGGGGAGCTGTCCTGCAACTCAACAGTAACC

Ser Ile Ile Ala Asn Ile Asp Trp Gln Asn Asn Asn Gln Thr Asn
AGCATAATTGCTAACATTGACTGGCAAAACAATAATCAGACAAAC

Ile Thr Phe Ser Ala Glu Val Ala Glu Leu Tyr Arg Leu Glu Leu
ATTACCTTTAGTGCAGAGGTGGCAGAACTATACAGATTGGAGTTG
1400

-continued

Envelope sequence

Gly Asp Tyr Lys Leu Val Glu Ile Thr Pro Ile Gly Phe Ala Pro
GCAGATTATAAATTGGTAGAAATAACACCAATTGGCTTCGCACCT

Thr Lys Glu Lys Arg Tyr Ser Ser Ala His Gly Arg His Thr Arg
ACAAAAGAAAAAAGATACTCCTCTGCTCACGGGAGACATACAAGA
1500

Gly Val Phe Val Leu Gly Phe Leu Gly Phe Leu Ala Thr Ala Gly
GGTGTGTTCGTGCTAGGGTTCTTGGGTTTTCTCGCAACAGCAGGT

Ser Ala Met Gly Ala Arg Ala Ser Leu Thr Val Ser Ala Gln Ser
TCTGCAATGGGCGCTCGAGCGTCCCTGACCGTGTCGGCTCAGTCC
1600

Arg Thr Leu Leu Ala Gly Ile Val Gln Gln Gln Gln Gln Leu Leu
CGGACTTTACTGGCCGGGATAGTGCAGCAACAGCAACAGCTGTTG

Asp Val Val Lys Arg Gln Gln Glu Leu Leu Arg Leu Thr Val Trp
GACGTGGTCAAGAGACAACAAGAACTGTTGCGACTGACCGTCTGG
1700

Gly Thr Lys Asn Leu Gln Ala Arg Val Thr Ala Ile Glu Lys Tyr
GGAACGAAAAACCTCCAGGCAAGAGTCACTGCTATAGAGAAGTAC

Leu Gln Asp Gln Ala Arg Leu Asn Ser Trp Gly Cys Ala Phe Arg
CTACAGGACCAGGCGCGGCTAAATTCATGGGGATGTGCGTTTAGA
1800

Gln Val Cys His Thr Thr Val Pro Trp Val Asn Asp Ser Leu Ala
CAAGTCTGCCACACTACTGTACCATGGGTTAATGATTCCTTAGCA

Pro Asp Trp Asp Asn Met Thr Trp Gln Glu Trp Glu Lys Gln Val
CCTGACTGGGACAATATGACGTGGCAGGAATGGGAAAAACAAGTC

Arg Tyr Leu Glu Ala Asn Ile Ser Lys Ser Leu Glu Gln Ala Gln
CGCTACCTGGAGGCAAATATCAGTAAAAGTTTAGAACAGGCACAA
1900

Ile Gln Gln Glu Lys Asn Met Tyr Glu Leu Gln Lys Leu Asn Ser
ATTCAGCAAGAGAAAAATATGTATGAACTACAAAAATTAAATAGC

Trp Asp Ile Phe Gly Asn Trp Phe Asp Leu Thr Ser Trp Val Lys
TGGGATATTTTTGGCAATTGGTTTGACTTAACCTCCTGGGTCAAG
2000

Tyr Ile Gln Tyr Gly Val Leu Ile Ile Val Ala Val Ile Ala Leu
TATATTCAATATGGAGTGCTTATAATAGTAGCAGTAATAGCTTTA

Arg Ile Val Ile Tyr Val Val Gln Met Leu Ser Arg Leu Arg Lys
AGAATAGTGATATATGTAGTACAAATGTTAAGTAGGCTTAGAAAG
2100

Gly Tyr Arg Pro Val Phe Ser Ser Pro Pro Gly Tyr Ile Gln ***
GGCTATAGGCCTGTTTTCTCTTCCCCCCCCGGTTATATCCAATAG

Ile His Ile His Lys Asp Arg Gly Gln Pro Ala Asn Glu Glu Thr
ATCCATATCCACAAGGACCGGGGACAGCCAGCCAACGAAGAAACA
2200

Glu Glu Asp Gly Gly Ser Asn Gly Gly Asp Arg Tyr Trp Pro Trp
GAAGAAGACGGTGGAAGCAACGGTGGAGACAGATACTGGCCCTGG

Pro Ile Ala Tyr Ile His Phe Leu Ile Arg Gln Leu Ile Arg Leu
GCGATAGCATATATACATTTCCTGATCCGCCAGCTGATTCGCCTC

Leu Thr Arg Leu Tyr Ser Ile Cys Arg Asp Leu Leu Ser Arg Ser
TTGACCAGACTATACAGCATCTGCAGGGACTTACTATCCAGGAGC
2300

-continued

Envelope sequence

Phe Leu Thr Leu Gln Leu Ile Tyr Gln Asn Leu Arg Asp Trp Leu
DTCCTGACCCTCCAACTCATCTACCAGAATCTCAGAGACTGGCTG

Arg Leu Arg Thr Ala Phe Leu Gln Tyr Gly Cys Glu Trp Ile Gln
AGACTTAGAACAGCCTTCTTGCAATATGGGTGCGAGTGGATCCAA
2400

Glu Ala Phe Gln Ala Ala Ala Arg Ala Thr Arg Glu Thr Leu Ala
GAAGCATTCCAGGCCGCCGCGAGGGCTACAAGAGAGACTCTTGCG

Gly Ala Cys Arg Gly Leu Trp Arg Val Leu Glu Arg Ile Gly Arg
GGCGCGTGCAGGGGCTTGTGGAGGGTATTGGAACGAATCGGGAGG
2500

Gly Ile Leu Ala Val Pro Arg Arg Ile Arg Gln Gly Ala Glu Ile
GGAATACTCGCGGTTCCAAGAAGGATCAGACAGGGAGCAGAAATC

Ala Leu Leu *** Gly Thr Ala Val Ser Ala Gly Arg Leu Tyr Glu
GCCCTCCTGTGAGGGACGGCAGTATCAGCAGGGAGACTTTATGAA
2600

Tyr Ser Met Glu Gly Pro Ser Ser Arg Lys Gly Glu Lys Phe Val
TACTCCATGGAAGGACCCAGCAGCAGAAAGGGAGAAAAATTTGTA

Gln Ala Thr Lys Tyr Gly
CAGGCAACAAAATATGGA

Gag sequence

Met Gly Ala Arg Asn Ser Val Leu Arg Gly Lys Lys Ala Asp Glu
ATGGGCGCGAGAAACTCCGTCTTGAGAGGGAAAAAAGCAGATGAA

Leu Glu Arg Ile Arg Leu Arg Pro Gly Gly Lys Lys Lys Tyr Arg
TTAGAAAGAATCAGGTTACGGCCCGGCGGAAAGAAAAAGTACAGG

Leu Lys His Ile Val Trp Ala Ala Asn Lys Leu Asp Arg Phe Gly
CTAAAACATATTGTGTGGGCAGCGAATAAATTGGACAGATTCGGA

100
Leu Ala Glu Ser Leu Leu Glu Ser Lys Glu Gly Cys Gln Lys Ile
TTAGCAGAGAGCCTGTTGGAGTCAAAAGAGGGTTGTCAAAAAATT

Leu Thr Val Leu Asp Pro Met Val Pro Thr Gly Ser Glu Asn Leu
CTTACAGTTTTAGATCCAATGGTACCGACAGGTTCAGAAAATTTA

200
Lys Ser Leu Phe Asn Thr Val Cys Val Ile Trp Cys Ile His Ala
AAAAGTCTTTTTAATACTGTCTGCGTCATTTGGTGCATACACGCA

Glu Glu Lys Val Lys Asp Thr Glu Gly Ala Lys Gln Ile Val Arg
GAAGAGAAAGTGAAAGATACTGAAGGAGCAAAACAAATAGTGCGG

300
Arg His Leu Val Ala Glu Thr Gly Thr Ala Glu Lys Met Pro Ser
AGACATCTAGTGGCAGAAACAGGAACTGCAGAGAAAATGCCAAGC

Thr Ser Arg Pro Thr Ala Pro Ser Ser Glu Lys Gly Gly Asn Tyr
ACAAGTAGACCAACAGCACCATCTAGCGAGAAGGGAGGAAATTAC

400
Pro Val Gln His Val Gly Gly Asn Tyr Thr His Ile Pro Leu Ser
CCAGTGCAACATGTAGGCGGCAACTACACCCATATACCGCTGAGT

Pro Arg Thr Leu Asn Ala Trp Val Lys Leu Val Glu Glu Lys Lys
CCCCGAACCCTAAATGCCTGGGTAAAATTAGTAGAGGAAAAAAAG

Phe Gly Ala Glu Val Val Pro Gly Phe Gln Ala Leu Ser Glu Gly
TTCGGGGCAGAAGTAGTGCCAGGATTTCAGGCACTCTCAGAAGGC

-continued

Gag sequence

500
Cys Thr Pro Tyr Asp Ile Asn Gln Met Leu Asn Cys Val Gly Asp
TGCACGCCCTATGATATCAACCAAATGCTTAATTGTGTGGGCGAC

His Gln Ala Ala Met Gln Ile Ile Arg Glu Ile Ile Asn Glu Glu
CATCAAGCAGCCATGCAGATAATCAGGGAGATTATCAATGAGGAA

600
Ala Ala Glu Trp Asp Val Gln His Pro Ile Pro Gly Pro Leu Pro
GCAGCAGAATGGGATGTGCAACATCCAATACCAGGCCCCTTACCA

Ala Gly Gln Leu Arg Glu Pro Arg Gly Ser Asp Ile Ala Gly Thr
GCGGGGCAGCTTAGAGAGCCAAGGGGATCTGACATAGCAGGGACA

700
Thr Ser Thr Val Glu Glu Gln Ile Gln Trp Met Phe Arg Pro Gln
ACAAGCACAGTAGAAGAACAGATCCAGTGGATGTTTAGGCCACAA

Asn Pro Val Pro Val Gly Asn Ile Tyr Arg Arg Trp Ile Gln Ile
AATCCTGTACCAGTAGGAAACATCTATAGAAGATGGATCCAGATA

800
Gly Leu Gln Lys Cys Val Arg Met Tyr Asn Pro Thr Asn Ile Leu
GGATTGCAGAAGTGTGTCAGGATGTACAACCCGACCAACATCCTA

Asp Ile Lys Gln Gly Pro Lys Glu Pro Phe Gln Ser Tyr Val Asp
GACATAAAACAGGGACCAAAGGAGCCGTTCCAAAGCTATGTAGAT

900
Arg Phe Tyr Lys Ser Leu Arg Ala Glu Gln Thr Asp Pro Ala Val
AGATTCTACAAAAGCTTGAGGGCAGAACAAACAGATCCAGCAGTG

Lys Asn Trp Met Thr Gln Thr Leu Leu Val Gln Asn Ala Asn Pro
AAGAATTGGATGACCCAAACACTGCTAGTACAAAATGCCAACCCA

Asp Cys Lys Leu Val Leu Lys Gly Leu Gly Met Asn Pro Thr Leu
GACTGTAAATTAGTGCTAAAAGGACTAGGGATGAACCCTACCTTA

1000
Glu Glu Met Leu Thr Ala Cys Gln Gly Val Gly Gly Pro Gly Gln
GAAGAGATGCTGACCGCCTGTCAGGGGCTAGGTGGGCCAGGCCAG

Lys Ala Arg Leu Met Ala Glu Ala Leu Lys Glu Val Ile Gly Pro
AAAGCTAGATTAATGGCAGAGGCCCTGAAAGAGGTCATAGGACCT

1100
Ala Pro Ile Pro Phe Ala Ala Ala Gln Gln Arg Lys Ala Phe Lys
GCCCCTATCCCATTCGCAGCAGCCCAGCAGAGAAAGGCATTTAAA

Cys Trp Asn Cys Gly Lys Glu Gly His Ser Ala Arg Gln Cys Arg
TGCTGGAACTGTGGAAAGGAAGGGCACTCGGCAAGACAATGCCGA

1200
Ala Pro Arg Arg Gln Gly Cys Trp Lys Cys Gly Lys Pro Gly His
GCACCTAGAAGGCAGGGCTGCTGGAAGTGTGGTAAGCCAGGACAC

Ile Met Thr Asn Cys Pro Asp Arg Gln Ala Gly Phe Leu Gly Leu
ATCATGACAAACTGCCCAGATAGACAGGCAGGTTTTTTAGGACTG

1300
Gly Pro Trp Gly Lys Lys Pro Arg Asn Phe Pro Val Ala Gln Val
GGCCCTTGGGGAAAGAAGCCCCGCAACTTCCCCGTGGCCCAAGTT

Pro Gln Gly Leu Thr Pro Thr Ala Pro Pro Val Asp Pro Ala Val
CCGCAGGGGCTGACACCAACAGCACCCCCAGTGGATCCAGCAGTG

Asp Leu Leu Glu Lys Tyr Met Gln Gln Gly Lys Arg Gln Arg Glu
GATCTACTGGAGAAATATATGCAGCAAGGGAAAAGACAGAGAGAG

1400
Gln Arg Glu Arg Pro Tyr Lys Glu Val Thr Glu Asp Leu Leu His
CAGAGAGAGAGACCATACAAGGAAGTGACAGAGGACTTACTGCAC

Leu Glu Gln Gly Glu Thr Pro Tyr Arg Glu Pro Pro Thr Glu Asp
CTCGAGCAGGGGGAGACACCATACAGGGAGCCACCAACAGAGGAC

-continued

Gag sequence

1500
Leu Leu His Leu Asn Ser Leu Phe Gly Lys Asp Gln
TTGCTGCACCTCAATTCTCTCTTTGGAAAAGACCAG

Example 6: Peptide Sequences Encoded By The ENV and GAG genes

The following coding regions for antigenic peptides, identified for convenience only by the nucleotide numbers of Example 5, within the env and gag gene regions are of particular interest.

env1 (1732-1809)

Arg Val Thr Ala Ile Glu Lys Tyr
AGAGTCACTGCTATAGAGAAGTAC

Leu Gln Asp Gln Ala Arg Leu Asn Ser Trp Gly Cys Ala Phe Arg
CTACAGGACCAGGCGCGGCTAAATTCATGGGGATGTGCGTTTAGA
1000
Gln Val Cys
CAAGTCTGC env2 (1912-1983)

Ser Lys Ser Leu Glu Gln Ala Gln
AGTAAAAGTTTAGAACAGGCACAA

Ile Gln Gln Glu Lys Asn Met Tyr Glu Leu Gln Lys Leu Asn Ser
ATTCAGCAAGAGAAAAATATGTATGAACTACAAAAATTAAATAGC
1940
Trp
TGG env3 (1482-1530)

Pro Thr Lys Glu Lys Arg Tyr Ser Ser Ala His Gly Arg His Thr Arg
CCTACAAAAGAAAAAAGATACTCCTCTGCTCACGGGAGACATACAAGA
1500 env4 (55-129)

Cys Thr Gln Tyr Val Thr Val Phe Tyr Gly Val Pro
TGCACCCAATATGTAACTGTTTTCTATGGCGTACCC

Thr Trp Lys Asn Ala Thr Ile Pro Leu Phe Cys Ala Thr
ACGTGGAAAAATGCAACCATTCCCCTGTTTTGTGCAACC
100 env5 (175-231)

Asp Asp
GATGAT

Tyr Gln Glu Ile Thr Leu Asn Val Thr Glu Ala Phe Asp Ala Trp
TATCAGGAAATAACTTTGAATGTAACAGAGGCTTTTGATGCATGG
200
Asn Asn
AATAAT env6 (274-330)

Glu Thr Ser Ile Lys Pro Gys Val Lys Lue Thr Pro Leu Cys
GAGACATCAATAAAACCATGTGTGAAACTAACACCTTTATGT
300
Val Ala Met Lys Cys
GTAGCAATGAAATGC env7 (607-660)

Asn His Cys Asn Thr Ser Val Ile
AACCATTGCAACACATCAGTCATC
610
Thr Glu Ser Cys Asp Lys His Tyr Trp Asp
ACAGAATCATGTGACAAGCACTATTGGGAT env8 (661-720)

-continued

Ala Ile Arg Phe Arg
GCTATAAGGTTTAGA

Tyr Cys Ala Pro Pro Gly Tyr Ala Leu Leu Arg Gys Asn Asp Thr
TACTGTGCACCACCGGGTTATGCCCTATTAAGATGTAATGATACC
700 env9 (997-1044)

Lys Arg Pro Arg Gln Ala Trp Cys Trp Phe Lys Gly Lys
AAAAGACCCAGACAAGCATGGTGCTGGTTCAAAGGCAAA
1000
Trp Lys Asp
TGGAAAGAC env10 (1132-1215)

Lys Gly Ser Asp Pro Glu Val Ala Tyr Met Trp Thr Asn
AAAGGCTCAGACCCAGAAGTAGCATACATGTGGACTAAC

Cys Arg Gly Glu Phe Leu Tyr Cys Asn Met Thr Trp Phe Leu Asn
TGCAGAGGAGAGTTTCTCTACTGCAACATGACTTGGTTCCTCAAT
1200 env11 (1237-1305)

Arg Asn Tyr Ala Pro Cys His Ile
CGCAATTATGCACCGTGCCATATA

Lys Gln Ile Ile Asn Thr Trp His Lys Val Gly Arg Asn Val Tyr
AAGCAAATAATTAACACATGGCATAAGGTAGGGAGAAATGTATAT
1300 gagl (99-1053)

Asp Cys Lys Leu Val Leu Lys Gly Leu Gly Met Asn Pro Thr Leu
GACTGTAAATTAGTGCTAAAAGGACTAGGGATGAACCCTACCTTA
1000
Glu Glu Met Leu Thr Ala
GAAGAGATGCTGACCGCC

Of the foregoing peptides, env1, env2, env3 and gag1 are particularly contemplated for diagnostic purposes, and env4, env5, env6, env7, env8, env9, env10 and env11 are particularly contemplated as protecting agents. These peptides have been selected in part been selected in part because of their sequence homology to certain of the envelope and gag protein products of other of the retroviruses in the HIV group. For vaccinating purposes, the foregoing peptides may be coupled to a carrier protein by utilizing suitable and well known techniques to enhance the host's immune response. Adjuvants such as calcium phosphate or alum hydroxide may also be added. The foregoing peptides can be synthesized by conventional protein synthesis techniques, such as that of Merrifield.

It will be apparent to those skilled in the art that various modifications and variations can be made in the processes and products of the present invention. Thus, it is intended that the present application cover the modifications and variations of this invention provided they come within the scope of the appended claims and their equivalents. For convenience in interpreting the following claims, the following table sets forth the correspondence between codon codes and amino acids and the correspondence between three-letter and one-letter amino acid symbols.

| | | DNA CODON | | | | AMINO ACID 3 LET. | | | | AMINO ACID 1 LET. | | | |
|---|---|---|---|---|---|---|---|---|---|---|---|---|---|
| | 2 | T | C | A | G | T | C | A | G | T | C | A | G |
| 1 | 3 | | | | | | | | | | | | |
| | T | TTT | TCT | TAT | TGT | PHE | SER | TYR | CYS | F | S | Y | C |
| T | C | TTC | TCC | TAC | TGC | PHE | SER | TYR | CYS | F | S | Y | C |
| | A | TTA | TCA | TAA | TGA | LEU | SER | *** | *** | L | S | * | * |
| | G | TTG | TCG | TAG | TGG | LEU | SER | *** | TRP | L | S | * | W |
| | T | CTT | CCT | CAT | CGT | LEU | PRO | HIS | ARG | L | P | H | R |
| C | C | CTC | CCC | CAC | CGC | LEU | PRO | HIS | ARG | L | P | H | R |
| | A | CTA | CCA | CAA | CGA | LEU | PRO | GLN | ARG | L | P | Q | R |
| | G | CTG | CCG | CAG | CGG | LEU | PRO | GLN | ARG | L | P | Q | R |
| | T | ATT | ACT | AAT | AGT | ILE | THR | ASN | SER | I | T | N | S |
| A | C | ATC | ACC | AAC | AGC | ILE | THR | ASN | SER | I | T | N | S |
| | A | ATA | ACA | AAA | AGA | ILE | THR | LYS | ARG | I | T | K | R |
| | G | ATG | ACG | AAG | AGG | MET | THR | LYS | ARG | M | T | K | R |
| | T | GTT | GCT | GAT | GGT | VAL | ALA | ASP | GLY | V | A | D | G |
| G | C | GTC | GCC | GAC | GGC | VAL | ALA | ASP | GLY | V | A | D | G |
| | A | GTA | GCA | GAA | GGA | VAL | ALA | GLU | GLY | V | A | E | G |
| | G | GTG | GCG | GAG | GGG | VAL | ALA | GLU | GLY | V | A | E | G |

3 Letter 1 Letter CODONS

-continued

| | | |
|---|---|---|
| ALA | A | GCT GCC GCA GCG |
| ARG | R | CGT CGC CGA CGG AGA AGG |
| ASN | N | AAT AAC |
| ASP | D | GAT GAC |
| CYS | C | TGT TGC |
| GLN | Q | CAA CAG |
| GLU | E | GAA GAG |
| GLY | G | GGT GGC GGA GGG |
| HIS | H | CAT CAC |
| ILE | I | ATT ATC ATA |
| LEU | L | CTT CTC CTA CTG TTA TTG |
| LYS | K | AAA AAG |
| MET | M | ATG |
| PHE | F | TTT TTC |
| PRO | P | CCT CCC CCA CCG |
| SER | S | TCT TCC TCA TCG AGT AGC |
| THR | T | ACT ACC ACA ACG |
| TRP | W | TGG |
| TYR | Y | TAT TAC |
| VAL | V | GTT GTC GTA GTG |
| *** | * | TAA TAG TGA |

What is claimed is:

1. A peptide comprising immunological properties of a first portion of the envelope glycoprotein of a HIV-2 virus, wherein said peptide comprises no more than about 40 amino acid residues, said first portion of the envelope glycoprotein is antigenic or is capable of eliciting the production of antibodies directed to the peptide alone or when conjugated to a carrier molecule, and said envelope glycoprotein comprises an amino acid sequence substantially as follows:

MetMetAsnGlnLeuLeuIleAlaIleLeuLeuAlaSerAlaCys

LeuValTyrCysThrGlnTyrValThrValPheTyrGlyValPro

ThrTrpLysAsnAlaThrIleProLeuPheCysAlaThrArgAsn

100
ArgAspThrTrpGlyThrIleGlnCysLeuProAspAsnAspAsp

TyrGlnGluIleThrLeuAsnValThrGluAlaPheAspAlaTrp

200
AsnAsnThrValThrGluGlnAlaIleGluAspValTrpHisLeu

PheGluThrSerIleLysProCysValLysLeuThrProLeuCys

300
ValAlaMetLysCysSerSerThrGluSerSerThrGlyAsnAsn

ThrThrSerLysSerThrSerThrThrThrThrThrProThrAsp

400
GlnGluGlnGluIleSerGluAspThrProCysAlaArgAlaAsp

AsnCysSerGlyLeuGlyGluGluGluThrIleAsnCysGlnPhe

AsnMetThrGlyLeuGluArgAspLysLysLysGlnTyrAsnGlu

500
ThrTrpTyrSerLysAspValValCysGluThrAsnAsnSerThr

AsnGlnThrGlnCysTyrMetAsnHisCysAsnThrSerValIle

600
ThrGluSerCysAspLysHisTyrTrpAspAlaIleArgPheArg

-continued

TyrCysAlaProProGlyTyrAlaLeuLeuArgCysAsnAspThr

700
AsnTyrSerGlyPheAlaProAsnCysSerLysValValAlaSer

ThrCysThrArgMetMetGluThrGlnThrSerThrTrpPheGly

800
PheAsnGlyThrArgAlaGluAsnArgThrTyrIleTyrTrpHis

GlyArgAspAsnArgThrIleIleSerLeuAsnLysTyrTyrAsn

900
LeuSerLeuHisCysLysArgProGlyAsnLysThrValLysGln

IleMetLeuMetSerGlyHisValPheHisSerHisTyrGlnPro

IleAsnLysArgProArgGlnAlaTrpCysTrpPheLysGlyLys

1000
TrpLysAspAlaMetGlnGluValLysThrLeuAlaLysHisPro

ArgTyrArgGlyThrAsnAspThrArgAsnIleSerPheAlaAla

1100
ProGlyLysGlySerAspProGluValAlaTyrMetTrpThrAsn

CysArgGlyGluPhsLeuTyrCysAsnMetThrTrpPheLeuAsn

1200
TrpIleGluAsnLysThrHisArgAsnTyrAlaProCysHisIle

LysGlnIleIleAsnThrTrpHisLysValGlyArgAsnValTyr

1300
LeuProProArgGluGlyGluLeuSerCysAsnSerThrValThr

SerIleIleAlaAsnIleAspTrpGlnAsnAsnAsnGlnThrAsn

IleThrPheSerAlaGluValAlaGluLeuTyrArgLeuGluLeu

1400
GlyAspTyrLysLeuValGluIleThrProIleGlyPheAlaPro

ThrLysGluLysArgTyrSerSerAlaHisGlyArgHisThrArg

1500
GlyValPheValLeuGlyPheLeuGlyPheLeuAlaThrAlaGly

-continued

SerAlaMetGlyAlaArgAlaSerLeuThrValSerAlaGlnSer

1600
ArgThrLeuLeuAlaGlyIleValGlnGlnGlnGlnGlnLeuLeu

AspValValLysArgGlnGlnGluLeuLeuArgLeuThrValTre

1700
GlyThrLysAsnLeuGlnAlaArgValThrAlaIleGluLysTyr

LeuGlnAspGlnAlaArgLeuAsnSerTrpGlyCysAlaPkeArg

1800
GlnValCysHisThrThrValProTrpValAsnAspSerLeuAla

ProAspTrpAspAsnMetThrTrpGlnGluTrpGluLysGlnVal

ArgTyrLeuGluAlaAsnIleSerLysSerLeuGluGlnAlaGln

1900
IleGlnGlnGluLysAsnMetTyrGluLeuGlnLysLeuAsnSer

TrpAspIlePheGlyAsnTrpPheAspLeuThrSerTrpValLys

2000
TyrIleGlnTyrGlyValLeuIleIleValAlaValIleAlaLeu

ArgIleValIleTyrValValGlnMetLeuSerArgLeuArgLys

2100
GlyTyrArgProValPheSerSerProProGlyTyrIleGln***

IleHisIleHisLysAspArgGlyGlnProAlaAsnGluGluThr

2200
GluGluAspGlyGlySerAsnGlyGlyAspArgTyrTrpProTrp

ProIleAlaTyrIleHisPheLeuIleArgGlnLeuIleArgLeu

LeuThrArgLeuTyrSerILeCysArgAspLeuLeuSerArgSer

2300
PheLeuThrLeuGlnLeuIleTyrGlnAsnLeuArgAspTrpLeu

ArgLeuArgThrAlaPheLeuGlnTyrGlyCysGluTrpIleGln

2400
GluAlaPheGlnAlaAlaAlaArgAlaThrArgGluThrLeuAla

GlyAlaCysArgGlyLeuTrpArgValLeuGluArgIleGlyArg

2500
GlyIleLeuAlaValProArgArgIleArgGlnGlyAlaGluIle

AlaLeuLeu***GlyThrAlaValSerAlaGlyArgLeuTyrGlu

2600
TyrSerMetGluGlyProSerSerArgLysGlyGluLysPheVal

GlnAlaThrLysTyrGly.

2. A peptide according to claim 1, comprising an amino acid sequence of either of the following formulas:

XR--A-E-YL-DQ--L--WGC-----CZ

XA-E-YL-DZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of either of the following peptide sequences:

RVTAIEKYLQDQARLNSWGCAFRQVC, or

AIEKYLQDQ.

3. A peptide according to claim 1, comprising an amino acid sequence of either of the following formulas:

X--E--Q-QQEKN--EL--L---Z, or

XQ-QQEKNZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from those which permit the conservation of the immunological properties of either of the following peptide sequences:

SKSLEQAQIQQEKNMYELQKLNSW, or

QIQQEKN.

4. A peptide according to claim 1, comprising an amino acid sequence of either of the following formulas:

XEL--YK-V-I-P-G-APTK-KR-----Z, or

XYK-V-I-P-G-APTK-KRZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from those which permit the conservation of the immunological properties of either of the following peptide sequences:

ELGDYKLVEITPIGFAPTKEKRYSSAH, or

YKLVEITPIGFAPTKEK.

5. An antigenic composition comprising at least one peptide according to claims 2, 3, or 4, or at least an oligomer of the peptide that comprises the capability to specifically recognize the presence of anti-HIV-2 antibodies.

6. A peptide according to claim 1, comprising an amino acid sequence of one of the following formulas:

X---VTV-YGVP-WK-AT--LFCA-Z, or

XVTV-YGVP-WK-ATZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of either of the following peptide sequences:

CTQYVTVFYGVPTWKNATIPLFCAT, or

VTVFYGVPTWKNAT.

7. A peptide according to claim 6, comprising an amino acid sequence of one of the following formulas:

CTQYVTVFYGVPTWKNATIPLFCAT, or

VTVFYGVPTWKNAT.

8. A peptide according to claim 1, comprising an amino acid sequence of one of the following formulas:

X---QE--LNVTE-F--W-NZ, or

XLNVTE-FZ wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of the following peptide sequence:

DDYQEITLNVTEAFDAWNN.

9. A peptide according to claim 8, comprising an amino acid sequence of the following formula:

DDYQEITLNVTEAFDAWNN.

10. A peptide according to claim 1, comprising an amino acid sequence of one of the following formulas:

XL---S-KPCVKLTPLCV--KZ, or

XKPCVKLTPLCVZ, or

XS-KPCVKLTPLCVZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of the following peptide sequence:

ETSIKPCVKLTPLCVAMK.

11. A peptide according to claim 10, comprising an amino acid sequence of the following formula:

ETSIKPCVKLTPLCVAMK.

12. A peptide according to claim 1, comprising an amino acid sequence of one of the following formulas:

X---N-S-IT--C-Z, or

XN-S-ITZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of the following peptide sequence:

NHCNTSVITESCD.

13. A peptide according to claim 12, comprising an amino acid sequence of the following formula:

NHCNTSVITESCD.

14. A peptide according to claim 1, comprising an amino acid sequence of the following formula:

XYC-P-G-A-L-CN-TZ, wherein X and Z are OH or $NH_2$, or at least one of X and Z comprises a terminal group comprised from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of the following peptide sequence:

YCAPPGYALLRCNDT.

15. A peptide according to claim 14, comprising an amino acid sequence of the following formula:

YCAPPGLALLRCNDT.

16. A peptide according to claim 1, comprising an amino acid sequence of the following formula:

X-----A-C----W--Z wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacryl residue chosen from among those which permit the conservation of the immunological properties of the following peptide sequence:

NKRPRQAWCWFKGKWKD.

17. A peptide according to claim 16, comprising an amino acid sequence of the following formula:

NKRPRQAWCWFKGKWKD.

18. A peptide according to claim 1, comprising an amino acid sequence of one of the following formulas:

X-G-DPE-----NC-GEF-YCN-----NZ, or

XNC-GEF-YCNZ, wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permits the conservation of the immunological properties of either of the following peptide sequences:

KGSDPEVAYMWTNCRGEFLYCNMTWFLN, or

NCRGEFLYCN,

19. A peptide according to claim 18, comprising an amino acid sequence of one of the following formulas:

KGSDPEVAYMWTNCRGEFLYCNMTW-FLYN, or

MCRGEFLYCN.

20. A peptide according to claim 1, comprising an amino acid sequence of one of the following formulas:

X-----C-IKQ-I------G---YZ, or

XC-IKQ-IZ, wherein X and Z are OH or $NH_2$, or least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of either of the following peptide sequences:

RNYAPCHIKQIINTWHKVGRNVY, or or

CHIKQII.

21. A peptide according to claim 20, comprising an amino acid sequence of one of the following formulas:

RNYACHIKQIINTWHKVGRNVY, or or

CHIKQII.

22. An immunogenic composition comprising at least one peptide according to any one of the claims 6–21, or at least one oligomer of said peptide or said peptide conjugated to a carrier molecule, and a pharmacologically acceptable vehicle, wherein said immunogenic composition is suitable for injection into a warm blooded mannal, and said peptide is capable of eliciting antibody production against the peptide in sufficient quantities to form an effective immunocomplex with the entire HIV-2 retrovirus or with its corresponding proteins.

23. An immunogenic composition according to claim 22, wherein said immunogenic composition further comprises a second portion of the envelope glycoprotein of the HIV-2 virus, wherein said second portion and a portion of an envelope glycoprotein of HIV-1 have an amino acid homology of greater than 50%.

24. The antigenic peptide gag1 comprising an amino acid sequence of the following formula:

XNCKLVLKGLGMNPTLEEMLTAZ wherein X and Z are OH or $NH_2$, or at least one of X and Z comprises a terminal group comprising from one to five amino acid residues, provided that the immunological properties of the peptide having the terminal group shall not be essentially modified from the peptide lacking the terminal group, and wherein each of the hyphens corresponds to an aminoacyl residue chosen from among those which permit the conservation of the immunological properties of the following peptide sequence:

XNCKLVLKGLGMNPTLEEMLTA.

25. An antigenic composition comprising at least one gag1 peptide according to claim 24 or at least an oligomer of this peptide that comprises the capability to be recognized by human bological fluids such as serum containing anti-HIV-2 antibodies and under appropriate conditions anti-HIV-1 antibodies.

* * * * *